United States Patent [19]
Ishida et al.

[11] Patent Number: 6,040,407
[45] Date of Patent: Mar. 21, 2000

[54] CHAIN POLYENE GROUP-CONTAINING NORBORNENE COMPOUND AND UNSATURATED ETHYLENE COPOLYMER USING THE SAME

[75] Inventors: Tatsuyoshi Ishida; Masaaki Yasuda; Hitoshi Onishi; Noriaki Kihara; Toshiyuki Tsutsui, all of Yamaguchi; Toshihiro Sagane, Tokyo; Masaaki Kawasaki; Hidenari Nakahama, both of Ichihara, all of Japan

[73] Assignee: Mitsui Petrochemical Industrial, Ltd., Tokyo, Japan

[21] Appl. No.: 08/860,442

[22] PCT Filed: Dec. 25, 1995

[86] PCT No.: PCT/JP95/02655

§ 371 Date: Jun. 26, 1997

§ 102(e) Date: Jun. 26, 1997

[87] PCT Pub. No.: WO96/20150

PCT Pub. Date: Jul. 4, 1996

[30] Foreign Application Priority Data

Dec. 26, 1994 [JP] Japan ..................... 6-322099
Mar. 31, 1995 [JP] Japan ..................... 7-075288
May 25, 1995 [JP] Japan ..................... 7-126535

[51] Int. Cl.[7] .................................. C08F 10/02
[52] U.S. Cl. .................. 526/281; 526/159; 526/348; 585/23; 585/600
[58] Field of Search ............... 585/23, 600; 526/159, 526/281, 348

[56] References Cited

U.S. PATENT DOCUMENTS 3,674,755  7/1972  Yamamoto et al. ........... 260/80.78
3,676,512  7/1972  Arrighetti et al. ........... 260/666 PY
3,678,018  7/1972  Yasui et al. ................. 260/80.78
3,876,595  4/1975  Ogura et al. ................. 260/80.78
4,200,722  4/1980  Pennings et al. ............. 526/282
5,610,254  3/1997  Sagane et al. ............... 526/282

FOREIGN PATENT DOCUMENTS 71042365  12/1971  Japan .

*Primary Examiner*—David W. Wu
*Assistant Examiner*—Caixia Lu-Rutt

[57] ABSTRACT

The chain polyene-group containing norbornene compound of the invention is represented by the formula [I]:

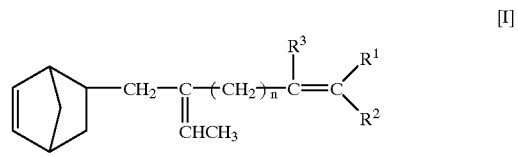

[I]

wherein n is an integer of 1 to 5, $R^1$ is an alkyl group of 1 to 5 carbon atoms, and $R^2$ and $R^3$ are each independently a hydrogen atom or an alkyl group of 1 to 5 carbon atoms.

The unsaturated ethylene copolymer of the invention is a random copolymer of 30 to 92% by mol of (i) ethylene units, 6 to 70% by mol of (ii) specific α-olefin units and 0.1 to 30% by mol of (iii) units derived from the norbornene compound [I], where the molar ratio of (i)/(ii) is in the range of 40/60 to 92/8 and the unit (iii) is represented by the specific formula, and has an intrinsic viscosity [η] of 0.05 to 10 dl/g.

The novel unsaturated ethylene copolymer is excellent in weathering resistance, heat resistance and ozone resistance and has a high vulcanizing rate.

10 Claims, No Drawings

CHAIN POLYENE GROUP-CONTAINING NORBORNENE COMPOUND AND UNSATURATED ETHYLENE COPOLYMER USING THE SAME

TECHNICAL FIELD

The present invention relates to a novel chain polyene group-containing norbornene compound and a process for preparing the compound. More particularly, the invention relates to a chain polyene group-containing norbornene compound suitably used for preparing a novel unsaturated ethylene copolymer being excellent in weathering resistance, heat resistance and ozone resistance and having a high vulcanizing rate, and to a process for preparing the compound.

Further, the invention relates to a novel unsaturated ethylene copolymer of the above properties using the chain polyene group-containing norbornene compound and to a process for preparing the copolymer.

Furthermore, the invention relates to a rubber composition containing the unsaturated ethylene copolymer.

BACKGROUND ART

Polyene compounds generally are compounds (monomers) having two or more carbon-to-carbon double bonds in one molecule, and many polyene compounds, e.g., 1,3-butadiene, 1,3-pentadiene, 1,4-hexadiene, ethylidene-2-norbornene and dicyclopentadiene, have been hitherto known.

When the polyene compounds are copolymerized with α-olefins such as ethylene and propylene, vulcanizable unsaturated ethylene copolymers can be obtained. Since the unsaturated ethylene copolymers generally have excellent weathering resistance, heat resistance and ozone resistance, they have been used for rubber products such as automotive industrial parts, industrial rubber products, insulating materials, building and civil engineering materials, and rubberized fabrics. Moreover, they have been widely used as blending materials for plastics such as polypropylene and polystyrene.

Examples of the unsaturated ethylene copolymers conventionally used include an ethylene/propylene/5-ethylidene-2-norbornene copolymer, an ethylene/propylene/dicyclopentadiene copolymer and an ethylene/propylene/1,4-hexadiene copolymer. Of these, the ethylene/propylene/5-ethylidene-2-norbornene copolymer has been particularly widely used, because it has a higher vulcanizing rate as compared with other unsaturated ethylene copolymers.

However, the conventional unsaturated ethylene copolymers are now desired to be further improved in the vulcanizing rate. That is, the unsaturated ethylene copolymers, for example, even the ethylene/propylene/5-ethylidene-2-norbornene copolymer, are low in the vulcanizing rate as compared with diene rubbers such as natural rubbers, styrene/butadiene rubber, isoprene rubber, butadiene rubber and nitrile rubber. Therefore, the co-vulcanizability of the unsaturated ethylene copolymers with the diene rubbers is insufficient.

Further, the vulcanizing rate of the unsaturated ethylene copolymers is lower than that of the diene rubbers, so that it is difficult to prepare vulcanized rubbers therefrom with high productivity by shortening the vulcanizing time, lowering the vulcanizing temperature or reducing the energy consumption in the vulcanization stage.

The vulcanizing rate of the unsaturated ethylene copolymers can be increased by increasing the amount of a vulcanizing agent used. However, if the unsaturated ethylene copolymers are vulcanized using a large amount of a vulcanizing agent, the vulcanizing agent sometimes blooms onto the surface of the resulting vulcanized rubbers, resulting in hygienic disadvantages.

Accordingly, development of a novel polyene compound capable of preparing an unsaturated ethylene copolymer being excellent in weathering resistance, heat resistance and ozone resistance and having a high vulcanizing rate, and development of an unsaturated ethylene copolymer using the polyene compound have been desired.

Under such circumstances mentioned above, the present inventors have earnestly studied polyene compounds and unsaturated ethylene copolymers using the polyene compounds. As a result, they have found that an unsaturated ethylene copolymer using a specific chain polyene group-containing norbornene compound, i.e., an unsaturated ethylene copolymer having constituent units derived from an α-olefin and a specific chain polyene group-containing norbornene compound and having an unsaturated bond, is excellent in weathering resistance, heat resistance and ozone resistance and has a high vulcanizing rate. Based on this finding, the present invention has been accomplished.

In Japanese Patent Publication No. 42365/1971, there is described a process for preparing an olefin copolymer comprising bringing at least one of ethylene and α-olefins having the formula $RCH=CH_2$ (R: hydrocarbon group having 1 to 20 carbon atoms) and a 5-polyenyl-2-norbornene compound into contact with a coordination catalyst, said 5-polyenyl-2-norbornene compound having the following formula:

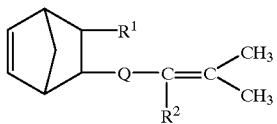

wherein $R^1$ and $R^2$ are each H or a hydrocarbon group of 1 to carbon atoms, and Q is a hydrocarbon group in which at least one internal double bond is situated at the non-conjugated position and all of the double bonds are of internal type.

However, the olefin copolymer obtained in the process of the above publication is not always sufficient under the circumstances that unsaturated copolymers being excellent in weathering resistance, heat resistance, ozone resistance and vulcanizing rate and having a good balance of these properties are desired.

The present invention is intended to solve such problems associated with the prior art as described above, and it is an object of the invention to provide a chain polyene group-containing norbornene compound suitably used for preparing an unsaturated ethylene copolymer being excellent in weathering resistance, heat resistance and ozone resistance and having a high vulcanizing rate, and to provide a process for preparing the compound.

It is another object of the invention to provide an unsaturated ethylene copolymer of the above properties and a process for preparing the copolymer.

It is a further object of the invention to provide a rubber composition containing the unsaturated ethylene copolymer.

DISCLOSURE OF THE INVENTION

The chain polyene group-containing norbornene compound according to the invention is represented by the formula [I]:

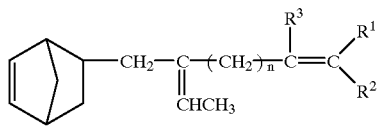

[I]

wherein n is an integer of 1 to 5, $R^1$ a hydrogen atom, or is an alkyl group of 1 to 5 carbon atoms, and $R^2$ and $R^3$ are each independently a hydrogen atom or an alkyl group of 1 to 5 carbon atoms, provided that $R^1$ and $R^2$ are not hydrogen at the same time.

The process for preparing a chain polyene group-containing norbornene compound according to the invention comprises:

reacting cyclopentadiene with a branched chain polyene compound represented by the formula [III]:

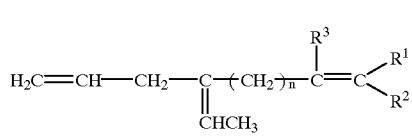

[III]

wherein n is an integer of 1 to 5, $R^1$ is an alkyl group of 1 to 5 carbon atoms, and $R^2$ and $R^3$ are each independently a hydrogen atom or an alkyl group of 1 to 5 carbon atoms, to thereby prepare the above-mentioned chain polyene group-containing norbornene compound.

The unsaturated ethylene copolymer according to the invention is characterized in that:

[A] said copolymer is a random copolymer of:
  (i) ethylene,
  (ii) an α-olefin of 3 to 20 carbon atoms, and
  (iii) at least one chain polyene group-containing norbornene compound represented by the above formula [I];

[B] said copolymer comprises:
  (i) constituent units derived from ethylene in an amount of 30 to 92% by mol,
  (ii) constituent units derived from the α-olefin of 3 to 20 carbon atoms in an amount of 6 to 70% by mol, and
  (iii) constituent units derived from the chain polyene group-containing norbornene compound represented by the above formula [I] in an amount of 0.1 to 30% by mol, wherein
  (iv) the molar ratio of (i) the constituent units derived from ethylene/(ii) the constituent units derived from the α-olefin of 3 to 20 carbon atoms is in the range of 40/60 to 92/8;

[C] the constituent unit derived from the chain polyene-group containing norbornene compound represented by the above formula [I] has a structure represented by the following formula [II]:

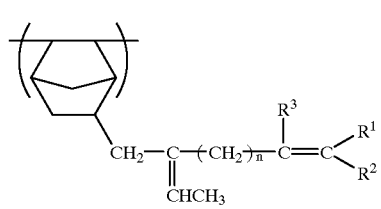

[II]

wherein n is an integer of 1 to 5, $R^1$ is an alkyl group of 1 to 5 carbon atoms, and $R^2$ and $R^3$ are each independently a hydrogen atom or an alkyl group of 1 to 5 carbon atoms; and

[D] said copolymer has an intrinsic viscosity [η], as measured in Decalin at 135° C., of 0.05 to 10 dl/g.

The process for preparing an unsaturated ethylene copolymer according to the invention comprises
copolymerizing
  (i) ethylene,
  (ii) an α-olefin of 3 to 20 carbon atoms, and
  (iii) at least one chain polyene group-containing norbornene compound represented by the above formula [I],
  in the presence of a catalyst formed from a transition metal compound, an organoaluminum compound and/or an ionizable ionic compound, to thereby prepare the above-mentioned unsaturated ethylene copolymer.

In addition to the chain polyene group-containing norbornene compound [I], at least one chain polyene group-containing norbornene compound [I-a] represented by the following formula [I-a] may be contained as the component (iii) of [A] in the unsaturated ethylene copolymer of the invention, in an amount smaller than that of the compound [I], preferably in an amount of less than 50% by mol, more preferably not more than 40% by mol, particularly preferably not more than 35% by mol, based on 100% by mol of the total amount of the compound [I] and the compound [I-a];

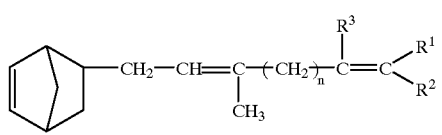

[I-a]

wherein, n, $R^1$, $R^2$ and $R^3$ have the same meanings as in the formula [I].

In this random copolymer, with reference to the above item [B] (iii), the total of the content of the constituent units [II] derived from the chain polyene group-containing norbornene compound represented by the formula [I] and the content of the later-described constituent units [II-a] derived from the chain polyene group-containing norbornere compound represented by the formula [I-a] is the same amount as in the case of using the chain polyene group-containing norbornene compound [II] alone, that is, 0.1 to 30% by mol.

The quantity ratio between the constituent units [II] and the constituent units [II-a] is in proportion to the quantity ratio between the chain polyene group-containing norbornene compounds [I] and [I-a]. The constituent units [II-a] are copolymerized in an amount of less than 50% by mol, preferably not more than 40% by mol, particularly preferably not more than 35% by mol, based on 100% by mol of the total of the constituent units [II] and [II-a].

With reference to the above item [C], the constituent unit derived from the chain polyene group-containing norbornene compound represented by the above formula [I] has a structure represented by the above formula [II], and the constituent unit derived from the chain polyene group-containing norbornene compound represented by the above formula [I-a] has a structure represented by the following formula [II-a]:

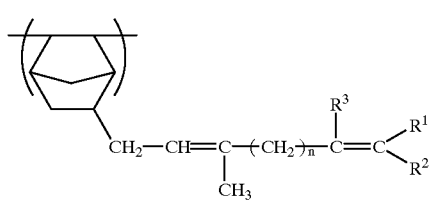

[II-a]

wherein n, $R^1$, $R^2$ and $R^3$ have the same meanings as in the formula [II].

The unsaturated ethylene copolymer of the invention can be prepared by copolymerizing (i) ethylene, (ii) an α-olefin of 3 to 20 carbon atoms, and (iii) at least one chain polyene group-containing norbornene compound represented by the above formula [I] and at least one chain polyene group-containing norbornene compound represented by the above formula [I-a] in a smaller amount than that of the chain polyene group-containing norbornene compound [I], in the presence of a catalyst formed from a transition metal compound, an organoaluminum compound and/or an ionizable ionic compound.

The rubber composition according to the invention comprises:

any of the above-mentioned unsaturated ethylene copolymers, and at least one component selected from the following components (a), (b) and (c):

(a) a reinforcing agent in an amount of not more than 300 parts by weight based on 100 parts by weight of the unsaturated ethylene copolymer, (b) a softener in an amount of not more than 200 parts by weight based on 100 parts by weight of the unsaturated ethylene copolymer, and (c) a vulcanizing agent.

The chain polyene group-containing norbornene compound according to the invention can be suitably used as a monomer copolymerizable with α-olefins such as ethylene and propylene when the unsaturated ethylene copolymer being excellent in weathering resistance, heat resistance and ozone resistance and having a high vulcanizing rate is prepared.

The unsaturated-ethylene copolymer according to the invention is excellent in weathering resistance, heat resistance and ozone resistance and has a high vulcanizing rate.

BEST MODE FOR CARRYING OUT THE INVENTION

The chain polyene group-containing norbornene compound, the process for preparing the norbornene compound, the unsaturated ethylene copolymer using the norbornene compound, the process for preparing the unsaturated ethylene copolymer and the rubber composition containing the unsaturated ethylene copolymer according to the invention are described in detail hereinafter.

Chain Polyene Group-containing Norbornene Compound

The chain polyene group-containing compound [I] according to the invention is represented by the following formula [I], as described above.

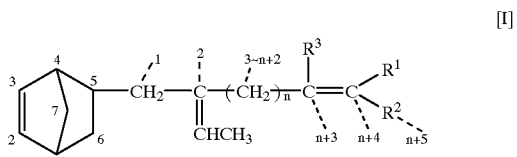

[I]

In the formula [I], n is an integer of 1 to 5, $R^1$ is an alkyl group of 1 to 5 carbon atoms, and $R^2$ and $R^3$ are each independently a hydrogen atom or an alkyl group of 1 to 5 carbon atoms. The numerals 1 to 7, n+3, etc. indicate carbon numbers (positions of substituents).

Examples of the alkyl groups of 1 to 5 carbon atoms include methyl, ethyl, n-propyl, i-propyl, n-butyl, i-butyl, sec-butyl, t-butyl, n-pentyl and i-pentyl.

Examples of the chain polyene group-containing norbornene compounds represented by the formula [I] (sometimes referred to as "chain polyene group-containing norbornene compound [I]" hereinafter) include the following compounds (1) to (24). Of these, the compounds (5), (6), (9), (11), (14), (19) and (20) are preferably employed.

(1) 5-(2-Ethylidene-4-hexenyl)-2-norbornene, (2) 5-(2-Ethylidene-5-methyl-4-hexenyl)-2-norbornene, (3) 5-(2-Ethylidene-5-methyl-4-heptenyl)-2-norbornene, (4) 5-(2-Ethylidene-5-ethyl-heptenyl)-2-norbornene, (5) 5-(2-Ethylidene-4,5-dimethyl-4-hexenyl)-2-norbornene, (6) 5-(2-Ethylidene-4,5-dimethyl-4-heptenyl)-2-norbornene, (7) 5-(2-Ethylidene-4-octenyl)-2-norbornene, (8) 5-(2-Ethylidene-5-methyl-4-octenyl)-2-norbornene, (9) 5-(2-Ethylidene-4-propyl-5-methyl-4-hexenyl)-2-norbornene,

(10) 5-(2-Ethylidene-5-heptenyl)-2-norbornene,

(11) 5-(2-Ethylidene-6-methyl-5-heptenyl)-2-norbornene,

(12) 5-(2-Ethylidene-6-nonenyl)-2-norbornene,

(13) 5-(2-Ethylidene-6-methyl-5-nonenyl)-2-norbornene,

(14) 5-(2-Ethylidene-5,6-dimethyl-5-heptenyl)-2-norbornene,

(15) 5-(2-Ethylidene-5,6-dimethyl-5-octenyl)-2-norbornene,

(16) 5-(2-Ethylidene-5,6-dimethyl-5-nonenyl)-2-norbornene,

(17) 5-(2-Ethylidene-5-ethyl-6-methyl-5-nonenyl)-2-norbornene,

(18) 5-(2-Ethylidene-5,6-diethyl-5-octenyl)-2-norbornene,

(19) 5-(2-Ethylidene-7-methyl-6-octenyl)-2-norbornene,

(20) 5-(2-Ethylidene-6,7-dimethyl-6-octenyl)-2-norbornene,

(21) 5-(2-Ethylidene-8-methyl-7-nonenyl)-2-norbornene,
(22) 5-(2-Ethylidene-7,8-dimethyl-7-nonenyl)-2-norbornene,
(23) 5-(2-Ethylidene-9-methyl-8-decenyl)-2-norbornene, and
(24) 5-(2-Ethylidene-8,9-dimethyl-8-decenyl)-2-norbornene.
The chemical formulas of the above compounds (1) to (24) are given below.
(1) 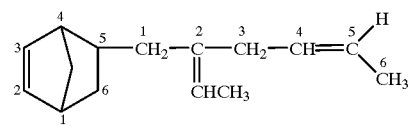
(2) 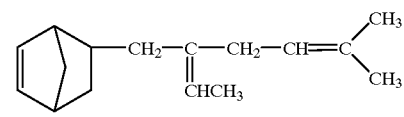
(3) 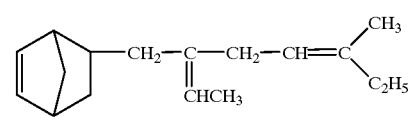
(4) 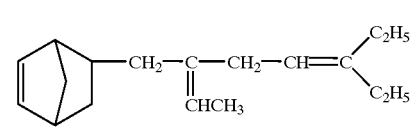
(5) 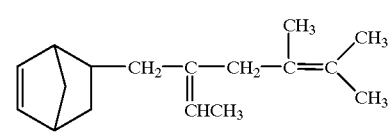
(6) 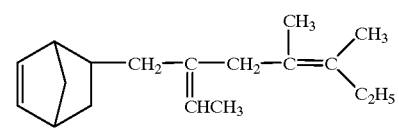
(7) 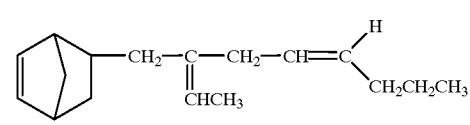
(8) 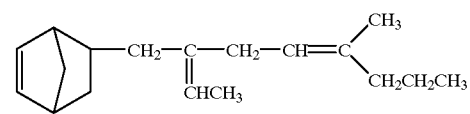
(9) 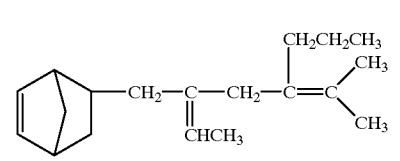
(10) 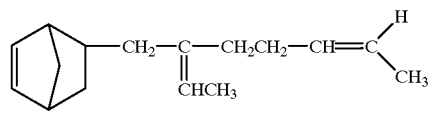
(11) 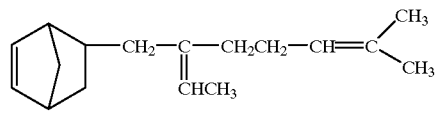
(12) 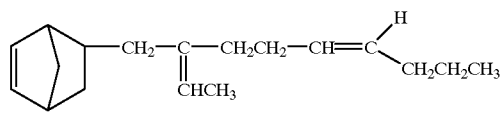
(13) 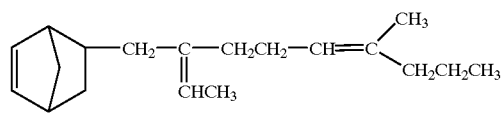
(14) 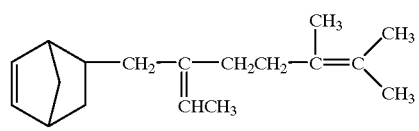
(15) 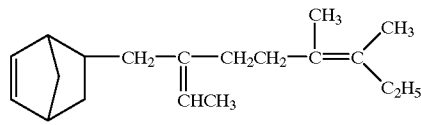
(16) 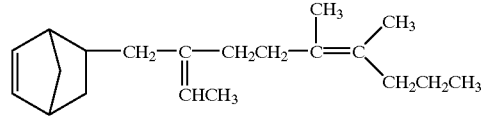
(17) 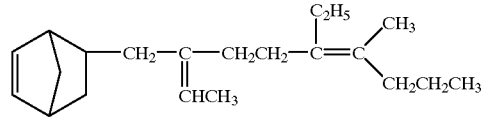
(18) 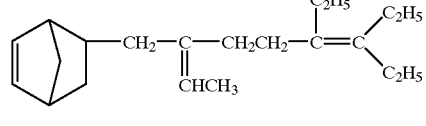
(19) 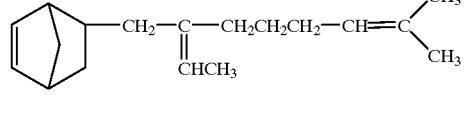
(20) 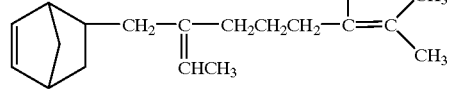

-continued

(21)
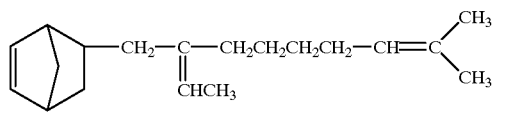

(22)
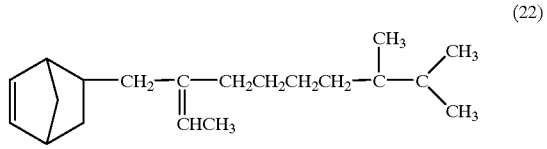

(23)
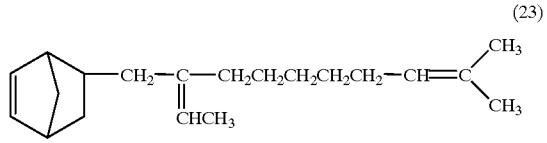

(24)
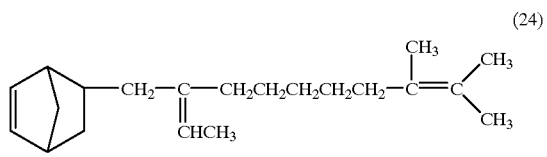

The chain polyene group-containing norbornene compound [I] is used as a monomer for preparing the later-described unsaturated ethylene copolymer, preferably used together with (i) ethylene and (ii) an α-olefin of 3 to 20 carbon atoms. In this case, the chain polyene group-containing norbornene compound [I] may be one kind of a stereoisomer, e.g., a trans form alone or a cis form alone, or it may be a mixture of stereoisomers, e.g., a mixture of a trans form and a cis form.

The chain polyene group-containing norbornene compound [I] can be suitably used for preparing novel unsaturated ethylene copolymers being excellent in weathering resistance, heat resistance and ozone resistance and having a high vulcanizing rate, as described later.

Next, the process for preparing the chain polyene group-containing norbornene compound [I] is explained.

Preparation of Chain Polyene Group-containing Norbornene Compound [i]

The process for preparing the chain polyene group-containing norbornene compound [I] (or the compound [I-a]) is described below in detail.

The chain polyene group-containing norborrene compound [I] of the invention is prepared by the following process.

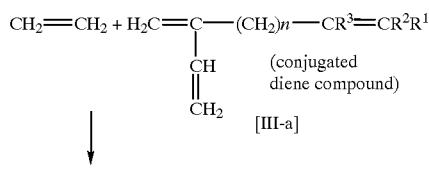

-continued

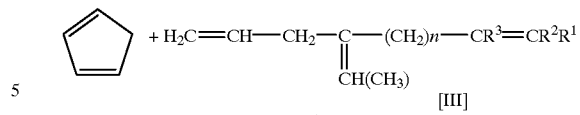

(branched chain polyene compound)

↓

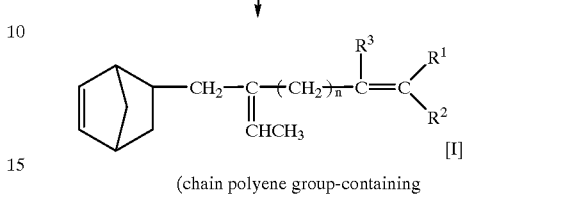

(chain polyene group-containing norbornene compound)

That is, as described in Japanese Patent Application No. 154952/1994 (filing date: Jul. 6, 1994) filed by the present applicant, ethylene is first reacted with a conjugated diene compound [III-a] represented by the following formula [III-a]:

[III-a]

$H_2C = C - (CH_2)_n - CR^3 = CR^2R^1$
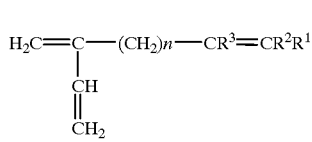

wherein, n is an integer of 1 to 5, $R^1$ is an alkyl group of 1 to 5 carbon atoms, and $R^2$ and $R^3$ are each independently a hydrogen atom or an alkyl group of 1 to 5 carbon atoms, in the presence of a catalyst comprising a transition metal compound and an organoaluminum compound so as to synthesize a branched chain polyene compound [III] represented by the following formula [III]:

[III]

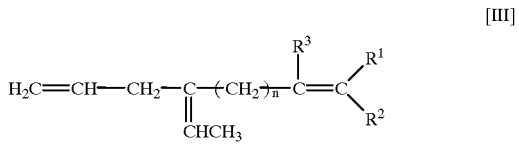

wherein, n, $R^1$, $R^2$ and $R^3$ have the same meanings as in the formula [III-a].

Then, the branched chain polyene compound [III] is reacted with cyclopentadiene (Diels-Alder reaction) as described in Japanese Patent Application No. 322099/1994 (filing date: Dec. 26, 1994), to thereby obtain the chain polyene group-containing norbornene compound [I].

The steps of the process for preparing the chain polyene-group containing norbornene compound [I] are described in more detail in order hereinafter.

Preparation of Branched Chain Polyene Compound [III]

The branched chain polyene compound [III] can be prepared by reacting a compound having conjugated diene and represented by the formula [III-a] (sometimes referred to as "conjugated diene compound [III-a]" hereinafter) with ethylene.

Examples of the-alkyl groups of 1 to 5 carbon atoms in the formula [III-a] are the same as those described above.

Examples of the conjugated diene compounds represented by the formula [III-a] include the following compounds (1) to (24).

(1) 3-Methylene-1,5-heptadiene,
(2) 6-Methyl-3-methylene-1,5-heptadiene,
(3) 6-Methyl-3-methylene-1,5-octadiene,
(4) 6-Ethyl-3-methylene-1,5-octadiene,
(5) 5,6-Dimethyl-3-methylene-1,5-heptadiene,
(6) 5,6-Dimethyl-3-methylene-1,5-octadiene,
(7) 3-Methylene-1,5-nonadiene,
(8) 6-Methyl-3-methylene-1,5-nonadiene,
(9) 6-Methyl-5-propyl-3-methylene-1,5-heptadiene,
(10) 3-Methylene-1,6-octadiene,
(11) 7-Methyl-3-methylene-1,6-octadiene,
(12) 3-Methylene-1,6-decadiene,
(13) 7-Methyl-3-methylene-1,6-decadiene,
(14) 6,7-Dimethyl-3-methylene-1,6-octadiene,
(15) 6,7-Dimethyl-3-methylene-1,6-nonadiene,
(16) 6,7-Dimethyl-3-methylene-1,6-decadiene,
(17) 7-Methyl-6-ethyl-3-methylene-1,6-decadiene,
(18) 6,7-Diethyl-3-methylene-1,6-nonadiene,
(19) 8-Methyl-3-methylene-1,7-nonadiene,
(20) 7,8-Dimethyl-3-methylene-1,7-nonadiene,
(21) 9-Methyl-3-methylene-1,8-decadiene,
(22) 8,9-Dimethyl-3-methylene-1,8-decadiene,
(23) 10-Methyl-3-methylene-1,9-undecadiene, and
(24) 9,10-Dimethyl-3-methylene-1,9-undecadiene.

Through the above reaction, the branched chain polyene compound [III] is generally obtained in the form of a mixture of a trans form and a cis form. The trans form and the cis form can be separated from each other by means of distillation, though depending on the structure of the branched chain polyene compound [III].

By the above reaction, a chain polyene compound represented by the following formula [III-b] is sometimes produced as a by-product together with the branched chain polyene compound [III].

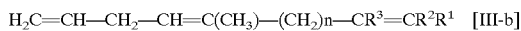

$$H_2C=CH-CH_2-CH=C(CH_3)-(CH_2)n-CR^3=CR^2R^1 \quad [III-b]$$

As the by-product, there may be mentioned, for example, 5,9-dimethyl-1,4,8-decatriene, which is produced as a by-product when 7-methyl-3-methylene-1,6-octadiene (β-myrcene) is reacted with ethylene to synthesize EMN (4-ethylidene-8-methyl-1,7-nonadiene).

The by-product can be usually separated by means of distillation.

The reaction of the conjugated diene compound [III-a] with ethylene is conducted for 0.5 to 30 hrs at a temperature of usually 50 to 200° C., preferably 70 to 150° C., under an ethylene pressure of 1 to 100 kg/cm$^2$, preferably 10 to 70 kg/cm$^2$, though these conditions vary depending on the type of the conjugated diene compound [III-a].

This reaction may be carried out in an atmosphere of an inert gas such as nitrogen or argon. The reaction can be carried out using no solvent, and however, it may be carried out in the presence of an inert hydrocarbon solvent such as hexane, heptane, octane, nonane, decane, undecane, dodecane, tridecane, toluene or xylene.

This reaction is generally carried out in the presence of a catalyst. Especially when the reaction is conducted in the presence of a catalyst comprising a transition metal compound and an organoaluminum compound, the branched chain polyene compound [III] can be efficiently obtained.

Examples of the transition metal compounds include chlorides of iron group transition metals, such as iron and ruthenium, cobalt group transition metals, such as cobalt, rhodium and iridium, and nickel group transition metals such as nickel and palladium, bromides of these metals, acetylacetonato salts, 1,1,1,5,5,5- hexafluoroacetylacetonato salts, and dipivaloylmethane salts. Of these, preferable are chlorides of cobalt, iron, nickel, rhodium and palladium, and particularly preferable is cobalt chloride.

In the reaction, these transition metal compounds (e.g., transition metal chlorides) can be used as they are, but they are preferably used in the form of transition metal complexes wherein organic ligands are coordinated to the transition metal compounds. In other words, it is preferable that an organic compound (coordination compound) capable of becoming a ligand of the transition metal is allowed to be present in the reaction system together with the transition metal compound, or a transition metal complex previously formed from the transition metal compound and the coordination compound is used.

Examples of the compounds capable of becoming the ligands include bis(diphenyphosphino)methane, 1,2-bis (diphenylphosphino)ethane, 1,3-bis(diphenylphosphino) propane, 1,4-bis(diphenylphosphino)butane, triethylphosphine, tributylphosphine, triphenylphosphine, cyclooctadiene and cyclooctatetraene.

As the complexes wherein organic ligands are coordinated to the transition metal compounds, preferably employable are [1,2-bis(diphenylphosphino)ethane]cobalt(II) chloride, [1,2-bis(diphenylphosphino)ethane]nickel(II) chloride, bis(triphenylphosphine)nickel(II) chloride, etc.

Examples of the organoaluminum compounds include those used in the preparation of the later-described unsaturated ethylene copolymer. Of these, triethylaluminum is preferably employed. The organoaluminum compound may be used as it is, or it can be used in the form of a toluene solution or a hexane solution.

In the reaction of the conjugated diene compound [III-a] with ethylene, the transition metal compound is used in an amount of preferably 0.001 to 10% by mol, particularly preferably 0.01 to 1% by mol, based on the conjugated diene compound [III-a]. The coordination compound is used in an amount of preferably 0 to 20 times by mol, particularly preferably 0.1 to 5 times by mol, as much as the transition metal compound.

The organoaluminum compound is used in an mount of preferably 1 to 200 times by mol, particularly preferably 3 to 100 times by mol, as much as the transition metal compound.

In the present invention, it is preferable that the transition metal compound (or transition metal complex) is previously contacted with the organoaluminum compound and the resulting product is used as the catalyst for the above reaction (reaction of the conjugated diene compound [III-a] and ethylene).

By virtue of the reaction of the conjugated diene compound [III-a] with ethylene, there can be obtained the following branched chain polyene compound [III]:

[III]

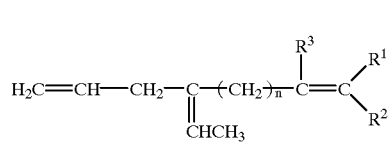

wherein n, R$^1$, R$^2$ and R$^3$ have the same meanings as in the aforesaid formula [III-a].

Examples of the branched chain polyene compounds [III] include the following compounds (1) to (24). Of these, the compounds (5), (6), (9), (11), (14), (19) and (20) are preferably employed.

(1) 4-Ethylidene-1,6-octadiene,
(2) 7-Methyl-4-ethylidene-1,6-octadiene,
(3) 7-Methyl-4-ethylidene-1,6-nonadiene,
(4) 7-Ethyl-4-ethylidene-1,6-nonadiene,
(5) 6,7-Dimethyl-4-ethylidene-1,6-octadiene,
(6) 6,7-Dimethyl-4-ethylidene-1,6-nonadiene,
(7) 4-Ethylidene-1,6-decadiene,
(8) 7-Methyl-4-ethylidene-1,6-decadiene,
(9) 7-Methyl-6-propyl-4-ethylidene-1,6-octadiene,
(10) 4-Ethylidene-1,7-nonadiene,
(11) 8-Methyl-4-ethylidene-1,7-nonadiene (EMN),
(12) 4-Ethylidene-1,7-undecadiene,
(13) 8-Methyl-4-ethylidene-1,7-undecadiene,
(14) 7,8-Dimethyl-4-ethylidene-1,7-nonadiene,
(15) 7,8-Dimethyl-4-ethylidene-1,7-decadiene,
(16) 7,8-Dimethyl-4-ethylidene-1,7-undecadiene,
(17) 8-Methyl-7-ethyl-4-ethylidene-1,7-undecadiene,
(18) 7,8-Diethyl-4-ethylidene-1,7-decadiene,
(19) 9-Methyl-4-ethylidene-1,8-decadiene,
(20) 8,9-Dimethyl-4-ethylidene-1,8-decadiene,
(21) 10-Methyl-4-ethylidene-1,9-undecadiene,
(22) 9,10-Dimethyl-4-ethylidene-1,9-undecadiene,
(23) 11-Methyl-4-ethylidene-1,10-dodecadiene, and
(24) 10,11-Dimethyl-4-ethylidene-1,10-dodecadiene.

The chemical formulas of the above compounds (1) to (24) are given below.

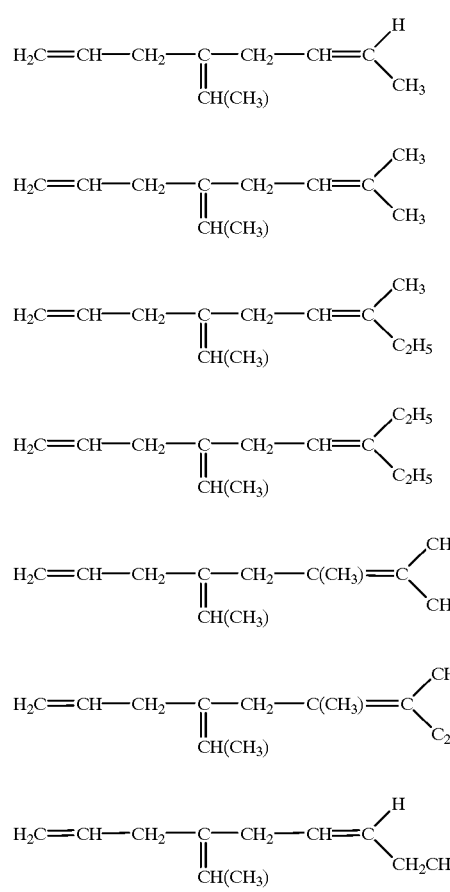

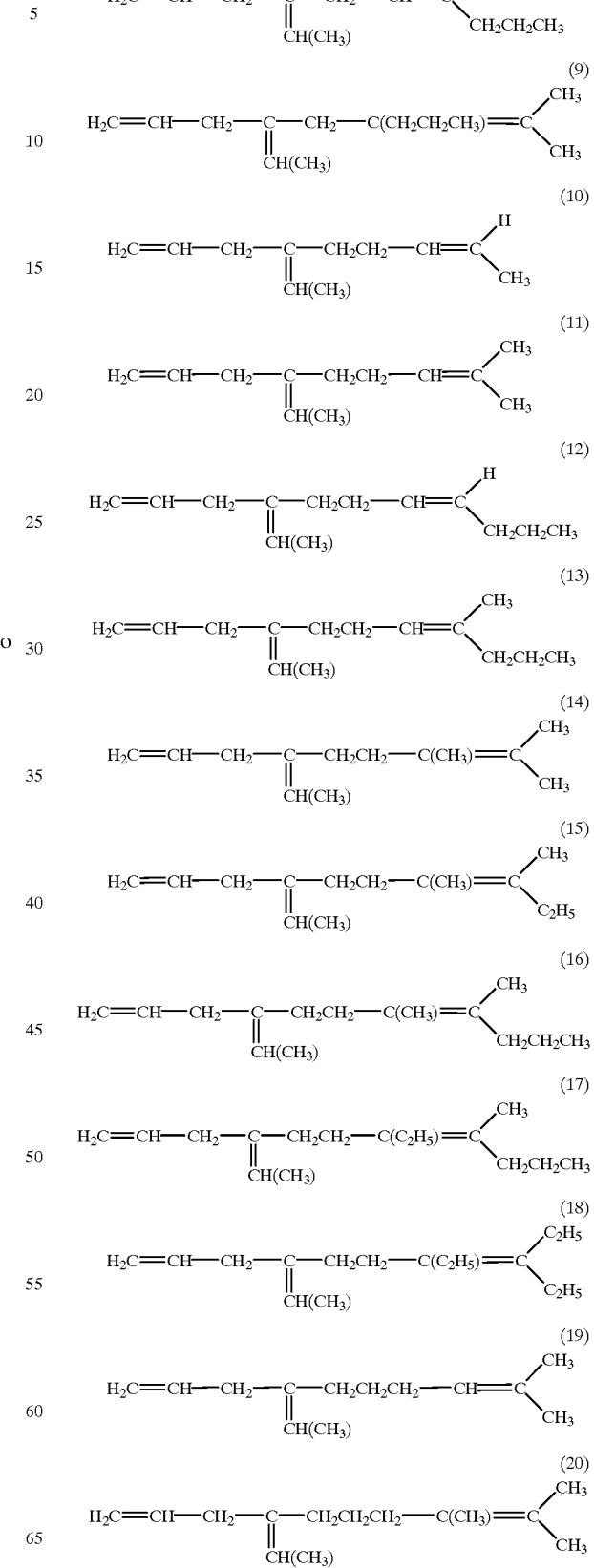

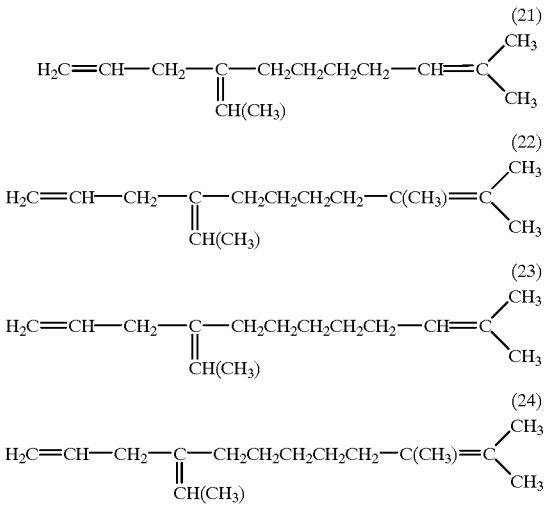

These branched chain polyene compounds [III] are used singly or in combination of two or more kinds in the preparation of the chain polyene group-containing norbornene compound [I].

The branched chain polyene compound [III] may be a mixture of a trans form and a cis form, or it may be a trans form alone or a cis form alone.

Preparation of Chain Polyene Group-containing Norbornene Compound [I]

In the present invention, the branched chain polyene compound [III] (also referred to as "non-conjugated triene compound") of the following formula [III]:

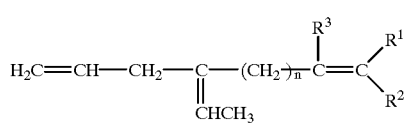

wherein, n, $R^1$, $R^2$ and $R^3$ have the same meanings as described above, is reacted with cyclopentadiene (Diels-Alder reaction) to obtain the chain polyene group-containing norbornene compound [I] of the following formula [I]:

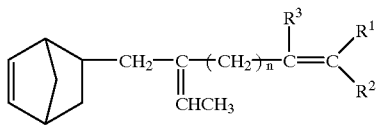

wherein, n is an integer of 1 to 5, $R^1$ is an alkyl group of 1 to 5 carbon atoms, and $R^2$ and $R^3$ are each independently a hydrogen atom or an alkyl group of 1 to 5 carbon atoms.

When $R^1$, $R^2$ or $R^3$ in the formula [I] is an alkyl group of 1 to 5 carbon atoms, examples of such alkyl groups include methyl, ethyl, n-propyl, isopropyl, n-butyl, isobutyl, sec-butyl, tert-butyl, n-pentyl and isopentyl.

In the branched chain polyene compound [III] used in the above reaction, $R^1$ and $R^2$ are each an alkyl group of 1 to 3 carbon atoms, particularly preferably methyl, and $R^3$ is preferably hydrogen.

The cyclopentadiene is generally obtained by subjecting dicyclopentadiene, i.e., a dimer of cyclopentadiene, to thermal decomposition distillation at a temperature of not lower than 160° C. Therefore, in the reaction of the cyclopentadiene with the branched chain polyene compound [III] in the present invention, dicyclopentadiene can be used in place of the cyclopentadiene depending on the reaction temperature used. That is, it is possible that the dicyclopentadiene is thermally decomposed in the reaction system to produce cyclopentadiene and this cyclopentadiene is used in the reaction with the branched chain polyene compound [III].

The reaction of the cyclopentadiene with the branched chain polyene compound [III] is carried out under the following conditions, though the conditions vary depending on the type of the branched chain polyene compound [III] used. 1 part by weight of the branched chain polyene compound [III] and 0.2 to 4 parts by weight, preferably 0.5 to 3 parts by weight, of the cyclopentadiene are stirred under heating at 50 to 250° C., preferably 100 to 200° C., under a pressure of 1 to 100 kg/cm², preferably 5 to 70 kg/cm², for about 0.5 to 30 hours, in an atmosphere of preferably an inert gas such as nitrogen or argon.

The reaction may be conducted in the presence of a radical polymerization inhibitor such as hydroquinone, if needed.

In the reaction of the cyclopentadiene with the branched chain polyene compound [III], a reaction solvent may be used or may not be used.

Examples of the reaction solvents employable herein include hydrocarbon type solvents, such as hexane, heptane, octane, nonane, decane, undecane, dodecane, tridecane, toluene and xylene; halogenated hydrocarbon type solvents, such as dichloromethane, dichloroethane and dichlorobenzene; ether type solvents, such as tetrahydrofuran and dioxane; and alcohol type solvents, such as methanol, ethanol, isopropanol and t-butanol. Water is also employable as the reaction solvent.

The chain polyene group-containing norbornene compound [I] obtained as above is represented by the aforesaid formula [I]. Examples of the chain polyene group-containing norbornene compounds [I] are described before.

The chain polyene group-containing norbornene compound [I] generally has a stereoisomeric structure (endo form and exo form based on the bonding way of chain polyene to the norbornene skeleton, and trans form and cis form based on the substitution way of double bond of the chain polyere).

The structure of the chain polyene group-containing norbornene compound [I] can be determined by mass spectrometry or measurement of infrared absorption spectrum, proton NMR spectrum, etc.

In the present invention, when the chain polyene group-containing norbornene compound [I] is used for preparing the later-described unsaturated ethylene copolymer and the rubber composition containing the copolymer, the compound [I] may be a mixture of the aforesaid various norbornene compounds having stereoisomeric structures or may be a compound of one stereoisomer only.

By the above reaction, the chain polyene group-containing norbornene compound [I] is usually obtained in the form of a mixture of an endo form and an exo form. The mixture can be separated by means of distillation according to necessity.

If the starting polyene compound used in the preparation of the chain polyene group-containing norbornene compound [I] contains in addition to the branched chain polyene compound [III] a by-product [III-b] of the following formula [III-b] produced during the synthesis of the branched chain polyene compound [III],

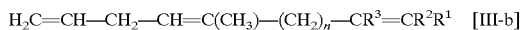

the by-product [III-b] is reacted with the cyclopentadiene to produce as a by-product a chain polyene group-containing norbornene compound [I-a] of the following formula [I-a]:

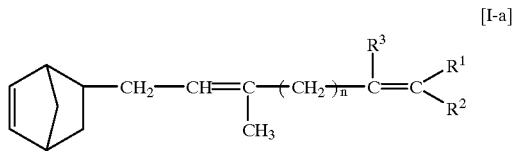

wherein, $R^1$, $R^2$, $R^3$ and n are the same as those in the formula [I].

In the process for preparing an unsaturated ethylene copolymer according to the invention, a substance containing a small amount of the chain polyene group-containing norbornene compound [I-a] in addition to the chain polyene group-containing norbornene compound [I] (i.e., mixture of the compound [I] and the compound [I-a]) may also be used, as described later.

Thus, when the substance containing the chain polyene group-containing norbornene compound [I-a] as the by-product in addition to the chain polyene group-containing norbornene compound [I] (mixture of the compound [I] and the compound [I-a]) is used as the chain polyene group-containing compound (iii) of [A] in the reaction with ethylene (i) and the α-olefin of 3 to 20 carbon atoms (ii), the resulting unsaturated ethylene copolymer contains the constituent units [II-a] derived from the norbornene compound [I-a] in addition to the constituent units [II] derived from the norbornene compound [I], as the constituent units derived from the chain polyene group-containing compound.

For example, when an EMHN-containing substance, which contains a small amount of a by-product [I-a] (5-[3,7-dimethyl-2,6-octadienyl]-2-norbornene) in addition to EMHN (5-(2-ethylidene-6-methyl-5-heptenyl)-2-norbornene), is used as the chain polyene group-containing norbornene compound [I], there can be obtained a product containing the following constituent unit [II'] derived from EMHN:

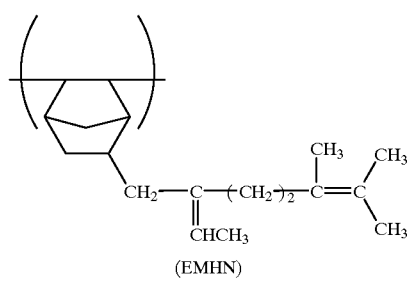

and the aforesaid amount (small amount) of the following constituent unit [II-a'] derived from the by-product [I-a]:

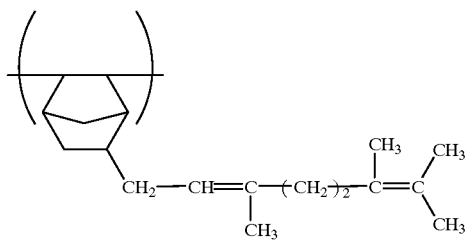

The chain polyene group-containing norbornene compound represented by the formula [I-a] can also be obtained by the process described in Japanese Patent Application No. 75288/1995 (filing date: Mar. 31, 1995).

That is, when cyclopentadiene is reacted with a chain non-conjugated triene compound represented by the following formula (a):

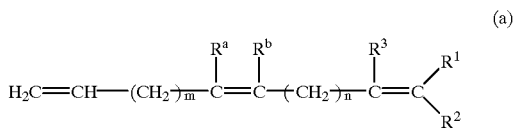

wherein, m and n are each independently an integer of 1 to 5, and $R^1$, $R^2$, $R^3$, $R^a$ and $R^b$ are each hydrogen or an alkyl group of 1 to 5 carbon atoms similarly to the case of the formula [I], provided that $R^1$, $R^2$ and $R^3$ do not represent hydrogen at the same time, there can be obtained a chain polyene group-containing norbornene compound represented by the following formula (b):

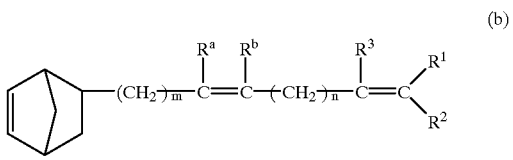

wherein, m, n, $R^1$, $R^2$, $R^3$, $R^a$ and $R^b$ have the same meanings as in the formula (a).

Next, the unsaturated ethylene copolymer of the invention containing the constituent units [II] derived from the chain polyene group-containing norbornene compound [I] and the process for preparing the copolymer are described.

Unsaturated Ethylene Copolymer

The unsaturated ethylene copolymer according to the invention is [A] a random copolymer of:
 (i) ethylene,
 (ii) an α-olefin of 3 to 20 carbon atoms, and
 (iii) the chain polyene group-containing norbornene compound [I].

The unsaturated ethylene copolymer of the invention may be [A] a random copolymer of (i) ethylene, (ii) an α-olefin of 3 to 20 carbon atoms, and (iii) the chain polyene group-containing norbornene compound [I] and the chain polyene group-containing norbornene compound [I-a] in a smaller amount than that of the chain polyene group-containing norbornene compound [I].

Examples of the α-olefins (ii) of 3 to 20 carbon atoms include propylene, 1-butene, 1-pentene, 1-hexene, 3-methyl- 1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene and 1-eicosene. Preferably used are propylene, 1-butene, 1-hexene and 1-octene. These α-olefins are used singly or in combination of two or more kinds.

As described above, the chain polyene group-containing norbornene compound [I] of the component (iii) is represented by the following formula [I].

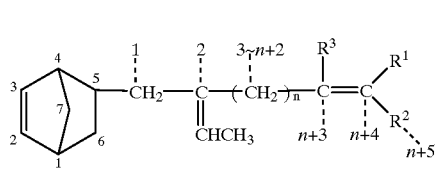

[I]

In the formula [I], n is an integer of 1 to 5, $R^1$ is an alkyl group of 1 to 5 carbon atoms, and $R^2$ and $R^3$ are each independently a hydrogen atom or an alkyl group of 1 to 5 carbon atoms. The numerals 1 to 7, n+3, etc. indicate carbon numbers (positions of substituents).

Examples of the alkyl groups of 1 to 5 carbon atoms include methyl, ethyl, n-propyl, i-propyl, n-butyl, i-butyl, sec-butyl, t-butyl, n-pentyl and i-pentyl.

Examples of the chain polyene group-containing norbornene compounds (iii) (chain polyene group-containing norbornene compound [I] represented by the formula [I] include the above-mentioned compounds (1) to (24). Preferably used are the compounds (5), (6), (9), (11), (14), (19) and (20).

These compounds are used singly or in combination of two or more kinds.

The chain polyene group-containing norbornene compound [I] used in the invention may be one kind of a stereoisomer, e.g., a trans form alone or a cis form alone, or it may be a mixture of stereoisomers, e.g., mixture of a trans form and a cis form.

In the unsaturated ethylene copolymer of the invention, the constituents units derived from each of the monomers of (i) ethylene, (ii) the α-olefin and (iii) the chain polyene group-containing norbornene compound (compound [I]) are arranged at random and bonded to each other, and the copolymer has a branched structure attributed to the chain polyene group-containing norbornene compound (iii). Moreover, the main chain of the copolymer is substantially linear. The substantially linear and crosslinked gel-free structure of the copolymer can be confirmed by the fact that this copolymer is soluble in organic solvents and does not substantially contain insoluble components. For example, it can be confirmed by the fact that the copolymer is perfectly dissolved in Decalin at 135° C. in measuring the intrinsic viscosity [η].

The unsaturated ethylene copolymer of the invention contains:
  (i) constituent units derived from the ethylene in an amount of 30 to 92% by mol, preferably 40 to 90% by mol, more preferably 45 to 90% by mol,
  (ii) constituent units derived from the α-olefin of 3 to 20 carbon atoms in an amount of 6 to 70% by mol, preferably 8 to 60% by mol, more preferably 10 to 55% by mol, and
  (iii) constituent units derived from the chain polyene group-containing norbornene compound [I] in an amount of 0.1 to 30% by mol, preferably 0.1 to 20% by mol, more preferably 0.2 to 10% by mol.

In particular, in the unsaturated ethylene copolymer of the invention, the constituent units (i) derived from ethylene and the constituent units (ii) derived from the α-olefin of 3 to 20 carbon atoms are present in a molar ratio ((i) ethylene/(ii) α-olefin) of 40/60 to 92/8, preferably 45/55 to 90/10, more preferably 50/50 to 88/12.

In the unsaturated ethylene copolymer of the invention, the constituent unit derived from the chain polyene group-containing norbornene compound [I] has a structure substantially represented by the following formula [II]:

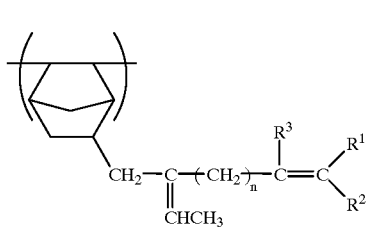

[II]

wherein n is an integer of 1 to 5, $R^1$ is an alkyl group of 1 to 5 carbon atoms, and $R^2$ and $R^3$ are each independently a hydrogen atom or an alkyl group of 1 to 5 carbon atoms.

The structure of this constituent unit derived from the chain polyene group-containing norbornene compound can be confirmed by measuring a $^{13}$C-NMR spectrum of the copolymer.

The unsaturated ethylene copolymer of the invention has an intrinsic viscosity [η], as measured in Decalin at 135° C., of 0.05 to 10 dl/g, preferably 0.1 to 7 dl/g, more preferably 0.2 to 5 dl/g.

In addition to the chain polyene group-containing norbornene compound [I], at least one chain polyene group-containing norbornene compound [I-a] represented by the following formula [I-a] may be contained as the component (iii) of [A] in the unsaturated ethylene copolymer of the invention, in a smaller amount than that of the compound [I], preferably in an amount of less than 50% by mol, more preferably not more than 40% by mol, particularly preferably 35% by mol, based on 100% by mol of the compound [I] and [I-a].

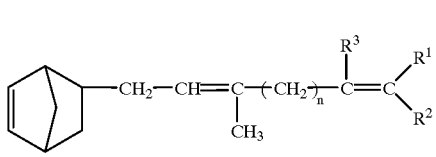

[I-a]

In the formula [I-a], n, $R^1$, $R^2$ and $R^3$ have the same meanings as in the formula [I].

The chain polyene group-containing norbornene compound [I-a] is obtained as a by-product during, for example, a process for synthesizing the chain polyene group-containing norbornene compound [I].

Such a random copolymer as mentioned above has the property [B] (iii): the total amount ([II]+[II-a]) of the constituent units [II] derived from the chain polyene group-containing norbornene compound represented by the formula [I] and the constituent units [II-a] derived from the chain polyene group-containing norbornene compound represented by the formula [I-a] is in the same range as in the case of the constituent units [II] derived from the chain polyene group-containing norbornene compound alone. That is, [II]+[II-a] is equal to 0.1 to 30% by mol, preferably 0.1 to 20% by mol, more preferably 0.2 to 10% by mol.

The copolymerization ratio between the constituent units [II] and the constituent units [II-a] corresponds to the molar ratio between the chain polyene group-containing norbornene compounds [I] and [I-a]. In other words, in the total (100% by mol) of the constituent units [II] and the constituent units [II-a], the constituent units [II-a] are copolymerized in an amount of less than 50% by mol, preferably not more than 40% by mol, more preferably not more than 35% by mol.

This random copolymer has the property [C]: the constituent unit derived from the chain polyene group-containing norbornene compound represented by the formula [I] has a structure represented by the formula [II] as described above, and the constituent unit derived from the chain polyene group-containing norbornene compound represented by the formula [I-a] has a structure represented by the following formula [II-a]:

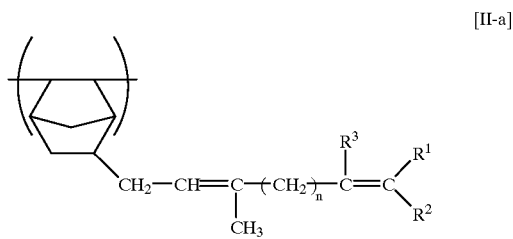

[II-a]

wherein n, $R^1$, $R^2$ and $R^3$ have the same meanings as in the formula [II].

Other properties of the copolymer (e.g., (i) amounts of ethylene constituent units (% by mol), (ii) ethylene constituent unit/α-olefin constituent unit (molar ratio), intrinsic viscosity of copolymer, etc.) are the same as those in the copolymer not containing the constituent unit [II-a].

The term "chain polyene group-containing norborene compound" used herein means both of the chain polyene group-containing norbornene compound [I] and the chain polyene group-containing norbornene compound [I-a], and the term "constituent unit derived from the chain polyene group-containing norbornene compound" used herein means both of the constituent unit [II] derived from the chain polyene group-containing norbornene compound [I] and the constituent unit [II-a] derived from the chain polyene group-containing norbornene compound [I-a], unless use of these terms does not depart from the objects of the invention.

The unsaturated ethylene copolymer of the invention is excellent in weathering resistance, heat resistance and ozone resistance and has a high vulcanizing rate.

The unsaturated ethylene copolymer of the invention may be used in the unvulcanized state or may be used after vulcanized by the later-described vulcanization process. If the copolymer is used after vulcanized, its properties are conspicuously exhibited.

The unsaturated ethylene copolymer is particularly preferably used as a resin modifier or for preparing various rubber products.

For example, when the unsaturated ethylene copolymer is added to polypropylene, polyethylene, polybutene, polystyrene, etc. as a resin modifier, their impact resistance and stress crack resistance are prominently improved.

The unsaturated ethylene copolymer of the invention may be vulcanized alone or co-vulcanized with other rubber materials.

Because of its high vulcanizing rate, the unsaturated ethylene copolymer can be vulcanized for a shorter period of time or at a lower temperature as compared with the conventional unsaturated ethylene copolymers, even if a large amount of a vulcanizing agent is rot used. Therefore, vulcanized rubbers can be produced with high productivity.

The unsaturated ethylene copolymer of the invention is excellent particularly in the co-vulcanizability with diene rubbers, such as natural rubber, styrene/butadiene rubber, isoprene rubber, butadiene rubber, nitrile rubber and chloroprene rubber, and the co-vulcanizates of the unsaturated ethylene copolymer and the diene rubbers not only has excellent mechanical properties, abrasion resistance, dynamic fatigue resistance and oil resistance, which are inherent in the diene rubbers, but also have excellent weathering resistance, ozone resistance and thermal aging resistance.

For example, a co-vulcanizate of the unsaturated ethylene copolymer of the invention and natural rubber has excellent strength, weathering resistance, ozone resistance and dynamic properties.

A co-vulcanizate of the unsaturated ethylene copolymer of the invention and nitrile rubber has excellent weathering resistance, ozone resistance and oil resistance.

A co-vulcanizate of the unsaturated ethylene copolymer of the invention and butadiene rubber has excellent weathering resistance, ozone resistance and abrasion resistance.

Preparation of Unsaturated Ethylene Copolymer

The unsaturated ethylene copolymer of the invention can be obtained by copolymerizing (i) ethylene, (ii) the α-olefin of 3 to 20 carbon atoms and (iii) the chain polyene group-containing norbornene compound [I] (and the chain polyene group-containing norbornene compound [I-a] in a smaller amount than that of the compound [I], according to necessity) in the presence of a catalyst.

As the catalyst, catalysts comprising compounds of transition metals such as vanadium (V), zirconium (Zr) and titanium (Ti), and organoaluminum compounds (organoaluminum oxy-compound) and/or an ionized ionic compound are employable, and particularly preferably used in the invention are (a) a catalyst comprising a soluble vanadium compound and an organoaluminum compound, and (b) a catalyst comprising a metallocene compound of a transition metal selected from elements of Group IVB of the periodic table and an organoaluminum oxycompound and/or an ionized ionic compound.

The soluble vanadium compound for forming the catalyst (a) is specifically represented by the following formula:

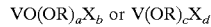

$VO(OR)_aX_b$ or $V(OR)_cX_d$ wherein R is a hydrocarbon group, X is a halogen atom, and a, b, c, d are numbers satisfying the conditions of $0 \leq a \leq 3$, $0 \leq b \leq 3$, $2 \leq a+b \leq 3$, $0 \leq c \leq 4$, $0 \leq d \leq 4$ and $3 \leq c+d \leq 4$.

Particular examples of the soluble vanadium compounds represented by the above formula include $VOCl_3$, $VO(OCH_3)Cl_2$, $VO(OC_2H_5)Cl_2$, $VO(OC_2H_5)_{1.5}Cl_{1.5}$, $VO(OC_2H_5)_2Cl$, $VO(O-n-C_3H_7)_{Cl2}$, $VO(O-iso-C_3H_7)Cl_2$, $VO(O-n-C_4H_9)Cl_2$, $VO(O-iso-C_4H_9)Cl_2$, $VO(O-sec-C_4H_9)Cl_2$, $VO(O-t-C_4H_9)Cl_2$, $VO(OC_2H_5)_3$, $VOBr_2$, $VCl_4$, $VOCl_2$, $VO(O-n-C_4H_9)_3$, and $VOCl_3 \cdot 2OC_8H_{17}OH$.

These compounds are used singly or in combination of two or more kinds.

The soluble vanadium compounds may be used in the form of electron donor addition products of the soluble vanadium compounds which can be obtained by contacting these soluble vanadium compounds with the following electron donors.

Examples of the electron donors include:

oxygen-containing electron donors, such as alcohols, phenols, ketones, aldehydes, carboxylic acids, organic acid halides, esters of organic acids or inorganic acids, ethers, diethers, acid amides, acid anhydrides and alkoxysilanes; and nitrogen-containing electron donors, such as ammonias, amines, nitrites, pyridines and isocyanates.

More specifically, there can be mentioned:

alcohols of 1 to 18 carbon atoms, such as methanol, ethanol, propanol, butanol, pentanol, hexanol, 2-ethylhexanol, octanol, dodecanol, octadecyl alcohol, oleyl alcohol, benzyl alcohol, phenylethyl alcohol, cumyl alcohol, isopropyl alcohol and isopropylbenzyl alcohol;

halogen-containing alcohols of 1 to 18 carbon atoms, such as trichloromethanol, trichloroethanol and trichlorohexanol;

phenols of 6 to 20 carbon atoms which may have alkyl groups, such as phenol, cresol, xylenol, ethylphenol, propylphenol, nonylphenol, cumylphenol and naphthol;

ketones of 3 to 15 carbon atoms, such as acetone, methyl ethyl ketone, methyl isobutyl ketone, acetophenone, benzophenone and benzoguinone;

aldehydes of 2 to 15 carbon atoms, such as acetaldehyde, propionaldehyde, octylaldehyde, benzaldehyde, tolualdehyde and naphthaldehyde;

organic acid esters of 2 to 18 carbon atoms, such as methyl formate, methyl acetate, ethyl acetate, vinyl acetate, propyl acetate, octyl acetate, cyclohexyl acetate, ethyl propionate, methyl butyrate, ethyl valerate, methyl chloroacetate, ethyl dichloroacetate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, methyl toluate, ethyl toluate, amyl toluate, ethyl ethylbenzoate, methyl anisate, ethyl anisate, ethyl ethoxybenzoate, γ-butyrolactone, δ-valerolactone, coumarin, phthalide and ethyl carbonate;

acid halides of 2 to 15 carbon atoms, such as acetyl chloride, benzoyl chloride, toluoyl chloride and anisoyl chloride;

ethers of 2 to 20 carbon atoms, such as methyl ether, ethyl ether, isopropyl ether, butyl ether, amyl ether, tetrahydrofuran, anisole and diphenyl ether;

acid anhydrides, such as acetic anhydride, phthalic anhydride and benzoic anhydride;

alkoxysilanes, such as ethyl silicate and diphenyldimethoxysilane;

acid amides, such as N,N-dimethylacetamide, N,N-diethylbenzamide and N,N-dimethyltoluamide;

amines, such as trimethylamine, triethylamine, tributylamine, tribenzylamine and tetramethylethylenediamine;

nitriles, such as acetonitrile, benzonitrile and tolunitrile; and pyridines, such as pyridine, methylpyridine, ethylpyridine and dimethylpyridine.

In the preparation of the electron donor addition products of the soluble vanadium compounds, the above electron donors may be used alone or in combination of two or more kinds.

In the present invention, the organoaluminum compound used for forming the catalyst (a) is represented by the following formula (III):

$$R^1{}_n AlX_{3-n} \quad (III)$$

wherein $R^1$ is a hydrocarbon group of 1 to 15, preferably 1 to 4 carbon atoms, X is a halogen atom or hydrogen, and n is 1 to 3.

The hydrocarbon group of 1 to 15 carbon atoms is, for example, an alkyl group, a cycloalkyl group or an aryl group, and particular examples include methyl, ethyl, n-propyl, isopropyl, isobutyl, pentyl, hexyl, octyl, cyclopentyl, cyclohexyl, phenyl and tolyl.

Examples of such organoaluminum compounds include:

trialkylaluminums, such as trimethylaluminum, triethylaluminum, triisopropylalumirum, triisobutylalumium, trioctylaluminum and tri-2-ethylhexylaluminum;

alkenylaluminums represented by the formula $(i\text{—}C_4H_9)_x Al_y(C_5H_{10})_z$ (x, y and z are each a positive number, and $z \geq 2x$), such as isoprenylaluminum;

trialkenylaluminums, such as triisopropenylaluminum;

dialkylaluminum halides, such as dimethylaluminum chloride, diethylaluminum chloride, diisopropylaluminum chloride, diisobutylaluminum chloride and dimethylaluminum bromide;

alkylaluminum sesquihalides, such as methylaluminum sesquichloride, ethylaluminum sesquichloride, isopropylaluminum sesquichloride, butylaluminum sesquichloride and ethylaluminum sesquibromide;

alkylaluminum dihalides, such as methylaluminum dichloride, ethylaluminum dichloride, isopropylalumium dichloride and ethylaluminum dibromide;

dialkylaluminum hydrides, such as diethylaluminum hydride and dibutylaluminum hydride; and alkylaluminum dihydrides, such as ethylaluminum dihydride and propylaluminum dihydride.

Also employable as the organoaluminum compound is a compound represented by the following formula (IV):

$$R^1{}_n AlY_{3-n} \quad (IV)$$

wherein $R^1$ is the same as in the above formula (III); Y is —$OR^{10}$ group, —$OSiR^{11}{}_3$ group, —$OAlR^{12}{}_2$ group, —$NR^{13}{}_2$ group, —$SiR^{14}{}_3$ group or —$N(R^{15})AlR^{16}{}_2$ group; $R^{10}$, $R^{11}$, $R^{12}$ and $R^{16}$ are each methyl, ethyl, isopropyl, isobutyl, cyclohexyl or phenyl; $R^{13}$ is hydrogen, methyl, ethyl, isopropyl, phenyl or trimethylsilyl; $R^{14}$ and $R^{15}$ are each methyl or ethyl; and n is 1 to 2.

The organoaluminum compounds represented by the formula (IV) include compounds of the following formulas wherein Me is methyl, Et is ethyl, Bu is butyl, and $R^1$ to $R^{16}$ are the same as those in the formula (IV).

(1) Compounds of the formula $R^1{}_n Al(OR^{10})_{3-n}$, e.g., dialkylaluminum alkoxides, such as dimethylaluminum methoxide, diethylaluminum ethoxide and diisobutylaluminum methoxide; partially alkoxylated alkylaluminums, such as ethylaluminum sesquiethoxide, butylaluminum sesquibutoxide and those having an average composition represented by, e.g., $R^1{}_{2.5}Al(OR^2)_{0.5}$; and partially alkoxylated and halogenated alkylaluminums, such as ethylaluminum ethoxychloride, butylaluminum butoxychloride and ethylaluminum ethoxybromide;

(2) Compounds of the formula $R^1{}_n Al(OSiR^{11}{}_3)_{3-n}$, e.g., $Et_2Al(OSiMe_3)$, $(iso-Bu)_2Al(OSiMe_3)$ and $(iso-Bu)_2Al(OSiEt_3)$;

(3) Compounds of the formula $R^1{}_n Al(OAlR^{12}{}_2)_{3-n}$, e.g., $Et_2AlOAlEt_2$ and $(iso-Bu)_2AlOAl(iso-Bu)_2$;

(4) Compounds of the formula $R^1{}_n Al(NR^{13}{}_2)_{3-n}$, e.g., $Me_2AlNEt_2$, $Et_2AlNHMe$, $Me_2AlNHEt$, $Et_2AlN(SiMe_3)_2$ and $(iso-Bu)_2AlN(SiMe_3)_2$;

(5) Compounds of the formula $R^1{}_n Al(SiR^{14}{}_3)_{3-n}$, e.g., $(iso-Bu)_2AlSiMe_3$; and (6) Compounds of the formula $R^1{}_n Al(N(R^{13})AlR^{16}{}_2)_{3-n}$, e.g., $Et_2AlN(Me)AlEt_2$ and $(iso-Bu)_2AlN(Et)Al(iso-Bu)_2$.

Of the above compounds, preferred are alkylaluminum halides, alkylaluminum dihalides or combinations thereof.

The organoaluminum compound used in the invention may contain an organometallic compound component of other metal than aluminum in a small amount.

Next, the catalyst (b) used in the invention, which comprises a metallocene compound and an organoaluminum oxy-compound or an ionized ionic compound, is described.

The metallocene compound of a transition metal selected from elements of Group IVB of the periodic table is represented by the following formula (V).

$$ML_x \qquad (V)$$

In the formula (V), M is a transition metal selected from elements of Group IVB of the periodic table, e.g., zirconium, titanium or hafnium, and x is a valence of the transition metal.

L is a ligand coordinated to the transition metal. At least one ligand L is a ligand having a cyclopentadienyl skeleton which may have a substituent.

Examples of the ligands having a cyclopentadienyl skeleton include alkyl or cycloalkyl substituted cyclopentadienyl groups, such as cyclopentadienyl, methylcyclopentadienyl, ethylcyclopentadienyl, n- or i-propylcyclopentadienyl, n-, i-, sec- or t-butylcyclopentadienyl, hexylcyclopentadienyl, octylcyclopentadienyl, dimethylcyclopentadienyl, trimethylcyclopentadienyl, tetramethylcyclopentadienyl, pentamethylcyclopentadienyl, methylethylcyclopentadienyl, methylpropylcyclopentadienyl, methylbutylcyclopentadienyl, methylhexylcyclopentadienyl, methylbenzylcyclopentadienyl, ethylbutylcyclopentadienyl, ethylhexylcyclopentadienyl and methylcyclohexylcyclopentadienyl.

Further, an indenyl group, a 4,5,6,7-tetrahydroindenyl group and a fluorenyl group can be also mentioned.

Those groups may be substituted with halogen atoms or trialkylsilyl groups.

Of the above ligands, particularly preferred are alkyl substituted cyclopentadienyl groups.

When the compound represented by the formula (V) has two or more ligands L having a cyclopentadienyl skeleton, two of the ligands having a cyclopentadienyl skeleton may be bonded to each other through an alkylene group such as ethylene or propylene, a substituted alkylene group such as isopropylidene and diphenylmethylene, a silylene group, or a substituted silylene group such as dimethylsilylene, diphenylsilylene or methylphenylsilylene.

Examples of L other than the ligand having a cyclopentadienyl skeleton include a hydrocarbon group of 1 to 12 carbon atoms, an alkoxyl group, an aryloxy group, a sulfonic acid-containing group ($-SO_3R^a$), a halogen atom or hydrogen atom, where Ra is an alkyl group, an alkyl group substituted with a halogen atom, an aryl group, or an aryl group substituted with a halogen atom or an alkyl group.

Examples of the hydrocarbon groups of 1 to 12 carbon atoms include alkyl groups, cycloalkyl groups, aryl groups and aralkyl groups, more specifically, there can be mentioned:

alkyl groups, such as methyl, ethyl, n-propyl, isopropyl, n-butyl, isobutyl, sec-butyl, t-butyl, pentyl, hexyl, octyl, decyl and dodecyl;

cycloalkyl groups, such as cyclopentyl and cyclohexyl;

aryl groups, such as phenyl and tolyl; and aralkyl group, such as benzyl and neophyl.

Examples of the alkoxy groups include methoxy, ethoxy, n-propoxy, isopropoxy, n-butoxy, isobutoxy, sec-butoxy, t-butoxy, pentoxy, hexoxy and octoxy.

The aryloxy group is, for example, phenoxy.

Examples of the sulfonic acid-containing group ($-SO_3R^a$) include methanesulfonato, p-toluenesulfonato, trifluoromethansulfonate and p-chlorobenzenesulfonato.

Examples of the halogen atoms include fluorine, chlorine, bromine and iodine.

The metallocene compound of the above formula wherein the valence of the transition metal is 4 is more specifically represented by the following formula (VI):

$$R^2{}_k R^3{}_l R^4{}_m R^5{}_n M \qquad (VI)$$

wherein M is the above-mentioned transition metal, $R^2$ is a group (ligand) having a cyclopentadienyl skeleton, $R^3$, $R^4$ and $R^5$ are each independently a group having a cyclopentadienyl skeleton or the same as L other than the ligand having a cyclopentadienyl skeleton in the above formula (V), k is an integer of not less than 1, and k+l+m+n=4.

Listed below are examples of the metallocene compounds containing zirconium as M and containing at least two ligands having a cyclopentadienyl skeleton.

Bis(cyclopentadienyl)zirconium monochloride monohydride,
Bis(cyclopentadienyl)zirconium dichloride,
Bis(cyclopentadienyl)zirconium dibromide,
Bis(cyclopentadienyl)methylzirconium monochloride,
Bis(cyclopentadienyl)zirconium phenoxymonochloride,
Bis(methylcyclopentadienyl)zirconium dichloride,
Bis(ethylcyclopentadienyl)zirconium dichloride,
Bis(n-propylcyclopentadienyl)zirconium dichloride,
Bis(isopropylcyclopentadienyl)zirconium dichloride,
Bis(t-butylcyclopentadienyl)zirconium dichloride,
Bis(n-butylcyclopentadienyl)zirconium dichloride,
Bis(sec-butylcyclopentadienyl)zirconium dichloride,
Bis(isobutylcyclopentadienyl)zirconium dichloride,
Bis(hexylcyclopentadienyl)zirconium dichloride,
Bis(octylcyclopentadienyl)zirconium dichloride,
Bis(indenyl)zirconium dichloride,
Bis(4,5,6,7-tetrahydroindenyl)zirconium dichloride,
Bis(indenyl)zirconium dibromide,
Bis(cyclopentadienyl)zirconium dimethyl,
Bis(cyclopentadienyl)zirconium methoxychloride,
Bis(cyclopentadienyl)zirconium ethoxychloride, Bis(fluorenyl)zirconium dichloride,
Bis(cyclopentadienyl)zirconiumbis(methanesulfonato),
Bis(cyclopentadienyl)zirconiumbis(p-toluenesulfonato),
Bis(cyclopentadienyl)zirconiumbis(trifluoromethane-sulfonato),
Bis(methylcyclopentadienyl)zirconiumbis(trifluoro-methanesulfonato),
Bis(ethylcyclopentadienyl)zirconiumbis(trifluoro-methanesulfonato),
Bis(propylcyclopentadienyl)zirconiumbis(trifluoro-methanesulfonato),
Bis(butylcyclopentadienyl)zirconiumbis(trifluoro-methanesulfonato),
Bis(hexylcyclopentadienyl)zirconiumbis(trifluoro-methanesulfonato),
Bis(1,3-dimethylcyclopentadienyl)zirconium-bis(trifluoromethanesulfonato),
Bis(1-methyl-3-ethylcyclopentadienyl)zirconium-bis(trifluoromethanesulfonato),
Bis(1-methyl-3-propylcyclopentadienyl)zirconium-bis(trifluoromethanesulfonato),
Bis(1-methyl-3-butylcyclopentadienyl)zirconium-bis(trifluoromethanesulfonato),
Bis(1,3-dimethylcyclopentadienyl)zirconium dichloride,
Bis(1-methyl-3-ethylcyclopentadienyl)zirconium dichloride,
Bis(1-methyl-3-propylcyclopentadienyl)zirconium dichloride,
Bis(1-methyl-3-butylcyclopentadienyl)zirconium dichloride,
Bis(1-methyl-3-hexylcyclopentadienyl)zirconium dichloride,
Bis(1-methyl-3-octylcyclopentadienyl)zirconium dichloride,
Bis(1-ethyl-3-butylcyclopentadienyl)zirconium dichloride,
Bis(trimethylcyclopentadienyl)zirconium dichloride,
Bis(tetramethylcyclopentadienyl)zirconium dichloride,
Bis(pentamethylcyclopentadienyl)zirconium dichloride,
Bis(methylbenzylcyclopentadienyl)zirconium dichloride,
Bis(ethylhexylcyclopentadienyl)zirconium dichloride, and
Bis(methylcyclohexylcyclopentadienyl)zirconium dichloride.

Also employable in the invention are those compounds wherein the 1,3-position substituted cyclopentadienyl group is replaced with a 1,2-position substituted cyclopentadienyl group.

Other examples are bridge type metallocene compounds of the above formula (VI) wherein at least two of $R^2$, $R^3$, $R^4$ and $R^5$, e.g., $R^2$ and $R^3$, are groups (ligands) having a cyclopentadienyl skeleton, and the at least two groups are bonded to each other through an alkylene group, a substituted alkylene group, a silylene group or a substituted silylene group. In these compounds, $R^4$ and $R^5$ are each independently the same as L other than the ligand having a cyclopentadienyl skeleton, as described in the formula (V).

Listed below are examples of such bridge type metallocene compounds.

Ethylenebis(indenyl)dimethylzirconium,
Ethylenebis(indenyl)zirconium dichloride,
Ethylenebis(indenyl)zirconiumbis(trifluoromethane-sulfonato),
Ethylenebis(indenyl)zirconiumbis(methanesulfonato),
Ethylenebis(indenyl)zirconiumbis(p-toluenesulfonato),
Ethylenebis(indenyl)zirconiumbis(p-chlorobenzenesulfonato),
Ethylenebis(4,5,6,7-tetrahydroindenyl)zirconium dichloride,
Isopropylidene(cyclopentadienyl-fluorenyl)zirconium dichloride,
Isopropylidene(cyclopentadienyl-methylcyclopentadienyl)zirconium dichloride,
Dimethylsilylenebis(cyclopentadienyl)zirconium dichloride,
Dimethylsilylenebis(methylcyclopentadienyl)zirconium dichloride,
Dimethylsilylenebis(dimethylcyclopentadienyl)zirconium dichloride,
Dimethylsilylenebis(trimethylcyclopentadienyl)-zirconium dichloride,
Dimethylsilylenebis(indenyl)zirconium dichloride,
Dimethylsilylenebis(indenyl)zirconiumbis(trifluoro-methanesulfonato),
Dimethylsilylenebis(4,5,6,7-tetrahydroindenyl)zirconium dichloride,
Dimethylsilylenebis(cyclopentadienyl-fluorenyl)zirconium dichloride,
Diphenylsilylenebis(indenyl)zirconium dichloride, and
Methylphenylsilylenebis(indenyl)zirconium dichloride Further, a metallocene compound of the following formula (A), which is described in Japanese Patent Laid-Open Publication No. 268307/1992, is also employable.

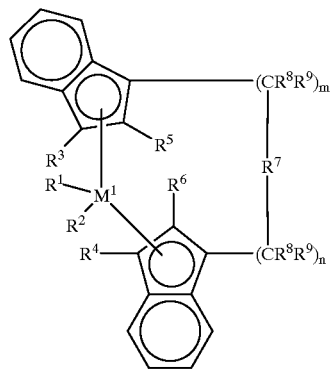

(A)

In the formula (A), $M^1$ is a metal of Group IVb, Vb or VIb of the periodic table, e.g., titanium, zirconium or hafnium.

$R^1$ and $R^2$ may be the same or different, and are each hydrogen, an alkyl group of 1 to 10, preferably 1 to 3 carbon atoms, an alkoxy group of 1 to 10, preferably 1 to 3 carbon atoms, an aryl group of 6 to 10, preferably 6 to 8 carbon atoms, an aryloxy group of 6 to 10, preferably 6 to 8 carbon atoms, an alkenyl group of 2 to 10, preferably 2 to 4 carbon atoms, an arylalkyl group of 7 to 40, preferably 7 to 10 carbon atoms, an alkylaryl group of 7 to 40, preferably 7 to 12 carbon atoms, an arylalkenyl group of 8 to 40, preferably 8 to 12 carbon atoms, or a halogen atom, preferably chlorine.

$R^3$ and $R^4$ may be the same or different, and are each hydrogen, a halogen atom, preferably fluorine, chlorine or bromine, an alkyl group of 1 to 10, preferably 1 to 4 carbon atoms which may be halogenated, an aryl group of 6 to 10, preferably 6 to 8 carbon atoms, or a group of $-NR_2^{10}$, —$SR^{10}$, —$OSiR_3{}^{10}$, —$SiR_3{}^{10}$ or —$PR_2{}^{10}$, where $R^{10}$ is a halogen atom, preferably chlorine, an alkyl group of 1 to 10, preferably 1 to 3 carbon atoms, or an aryl group of 6 to 10, preferably 6 to 8 carbon atoms.

$R^3$ and $R^4$ are each particularly preferably hydrogen. $R^5$ and $R^6$ may be the same or different, preferably the same, and have the same meanings as described for $R^3$ and $R^4$ with the proviso that each of $R^5$ and $R^6$ is not hydrogen. $R^5$ and $R^6$ are each preferably an alkyl group of 1 to 4 carbon atoms which may be halogenated, for example, methyl, ethyl, propyl, isopropyl, butyl, isobutyl or trifluoromethyl, preferably methyl.

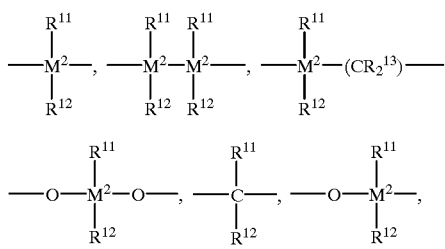

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$ $R^{12}$ and $R^{13}$ may be the same or different, and are each hydrogen, a halogen atom, an alkyl group of 1 to 10, preferably 1 to 4 carbon atoms, more preferably methyl, a fluoroalkyl group of 1 to 10 carbon atoms, preferably $CF_3$, an aryl group of 6 to 10, preferably 6 to 8 carbon atoms, a fluoroaryl group of 6 to 10 carbon atoms, preferably pentafluorophenyl, an alkoxy group of 1 to 10, preferably 1 to 4 carbon atoms, particularly preferably methoxy, an alkenyl group of 2 to 10, preferably 2 to 4 carbon atoms, an arylalkyl group of 7 to 40, preferably 7 to 10 carbon atoms, an arylalkenyl group of 8 to 40, preferably 8 to 12 carbon atoms, or an alkylaryl group of 7 to 40, preferably 7 to 12 carbon atoms, or $R^{11}$ and $R^{12}$, or $R^{11}$ and $R^{13}$ may form together with the carbon atoms to which they are bonded a ring.

$M^2$ is silicon, germanium or tin, preferably silicon or germanium.

$R^7$ is preferably =$CR^{11}R_{12}$, =$SiR^{11}R^{12}$, =$GeR^{11}R^{12}$, —O—, —S—, =SO, =$PR^{11}$ or =$P(O)R^{11}$.

$R^8$ and $R^9$ may be the same or different, and have the same meaning as described for $R^{11}$.

m and n may be the same or different, and are each 0, 1 or 2, preferably 0 or 1, and m+n is 0, 1 or 2, preferably 0 or 1.

Particularly preferred metallocene compounds satisfying the above conditions are compounds represented by the following formulas (i) to (iii).

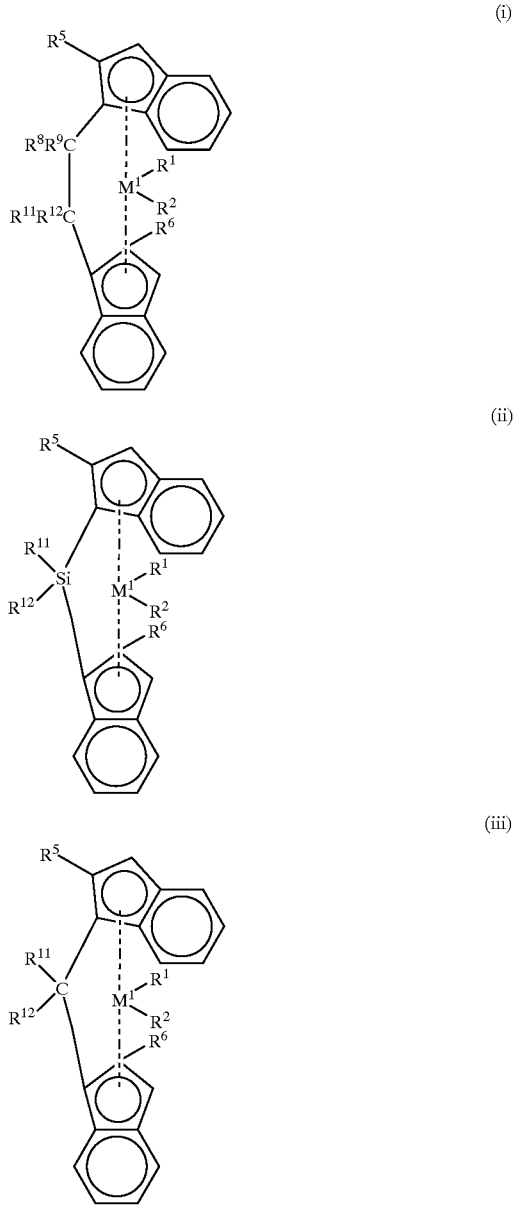

In the above formulas (i), (ii) and (iii), $M^1$ is Zr or Hf, $R^1$ and $R^2$ are each methyl or chlorine, $R^5$ and $R^6$ are each methyl, ethyl or trifluoromethyl, and $R^8$, $R^9$, $R^{10}$ and $R^{12}$ have the same meanings as described above.

Of the compounds represented by the formulas (i), (ii) and (iii), particularly preferred are the following compounds:

rac-ethylene(2-methyl-1-indenyl)$_2$-zirconium dichloride,
rac-dimethylsilylene (2-methyl-1-indenyl)$_2$-zirconium dichloride,
rac-dimethylsilylene(2-methyl-1-indenyl)$_2$-zirconium dimethyl,
rac-ethylene-(2-methyl-1-indenyl)$_2$-zirconium dimethyl,
rac-phenyl(methyl)silylene-(2-methyl-1-indenyl)$_2$-zirconium dichloride,
rac-diphenyl-silylene-(2-methyl-1-indenyl)$_2$-zirconium dichloride,
rac-methylethylene-(2-methyl-1-indenyl)$_2$-zirconium dichloride, and rac-dimethylsilylene-(2-ethyl-1-indenyl)$_2$-zirconium dichloride.

These metallocene compounds can be prepared by conventionally known processes (see, for example, Japanese Patent Laid-Open Publication No. 268307/1992).

In the present invention, a transition metal compound (metallocene compound) represented by the following formula (B) is also employable.

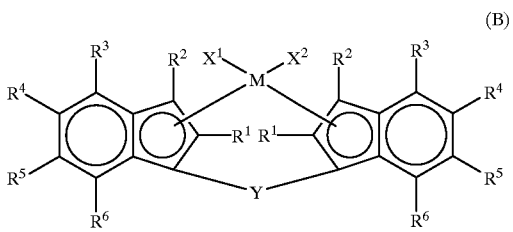
(B)

In the formula (B), M is a transition metal atom of Group IVa, Va or VIa of the periodic table, specifically, titanium, zirconium or hafnium.

$R^1$ and $R^2$ are each independently hydrogen, a halogen atom, a hydrocarbon group of 1 to 20 carbon atoms, a halogenated hydrocarbon group of 1 to 20 carbon atoms, a silicon-containing group, an oxygen-containing group, a sulfur-containing group, a nitrogen-containing group or a phosphorus-containing group.

Examples of the halogen atoms include fluorine, chlorine, bromine and iodine.

Examples of the hydrocarbon groups of 1 to 20 carbon atoms include alkyl groups, such as methyl, ethyl, propyl, butyl, hexyl, cyclohexyl, octyl, nonyl, dodecyl, eicosyl, norbornyl and adamantyl; alkenyl groups, such as vinyl, propenyl and cyclohexenyl; arylalkyl groups, such as benzyl, phenylethyl and phenylpropyl; and aryl groups, such as phenyl, tolyl, dimethylphenyl, trimethylphenyl, ethylphenyl, propylphenyl, biphenyl, naphthyl, methylnaphthyl, anthracenyl and phenanthryl.

Examples of the halogenated hydrocarbon groups include the above-exemplified hydrocarbon groups which are substituted with halogen atoms.

Examples of the silicon-containing groups include monohydrocarbon-substituted silyls, such as methylsilyl and phenylsilyl; dihydrocarbon-substituted silyls, such as dimethylsilyl and diphenylsilyl; trihydrocarbon-substituted silyls, such as trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl; silyl ethers of hydrocarbon-substituted silyls, such as trimethylsilyl ether; silicon-substituted alkyl groups, such as trimethylsilylmethyl; and silicon-substituted aryl groups, such as trimethylsililphenyl.

Examples of the oxygen-containing groups include hydroxy groups; alkoxy groups, such as methoxy, ethoxy, propoxy and butoxy; aryloxy groups, such as phenoxy, methylphenoxy, dimethylphenoxy and naphthoxy; and arylalkoxy groups, such as phenylmethoxy and phenylethoxy.

Examples of the sulfur-containing groups include those wherein oxygen is replaced with sulfur in the above-exemplified oxygen-containing group.

Examples of the nitrogen-containing groups include amino group; alkylamino groups, such as methylamino, dimethylamino, diethylamino, dipropylamino, dibutylamino and dicyclohexylamino; and arylamino or alkylarylamino groups, such as phenylamino, diphenylamino, ditolylamino, dinaphthylamino and methylphenylamino.

Examples of the phosphorus-containing groups include phosphino groups, such as dimethylphosphino and diphenylphosphino.

Of these, $R^1$ is preferably a hydrocarbon group, particularly preferably a hydrocarbon group of 1 to 3 carbon atoms (methyl, ethyl or propyl). $R^2$ is preferably hydrogen or a hydrocarbon group, particularly preferably hydrogen or a hydrocarbon group of 1 to 3 carbon atoms (methyl, ethyl or propyl).

$R^3$, $R^4$, $R^5$ and $R^6$ are each independently hydrogen, a halogen atom, a hydrocarbon group of 1 to 20 carbon atoms or a halogenated hydrocarbon group of 1 to 20 carbon atoms. Of these, preferred is hydrogen, the hydrocarbon group or the halogenated hydrocarbon group. At least one combination of $R^3$ and $R^4$, $R^4$ and $R^5$, or $R^5$ and $R^6$ may form together with the carbon atoms to which they are bonded a monocyclic aromatic ring.

When there are two or more hydrocarbon groups or halogenated hydrocarbon groups, excluding the groups for forming the aromatic ring, they may be bonded to each other to form a ring. When $R^6$ is a substituent other than the aromatic group, it is preferably hydrogen.

Examples of the halogen atoms, the hydrocarbon groups of 1 to 20 carbon atoms and the halogenated hydrocarbon groups of 1 to 20 carbon atoms are those described for $R^1$ and $R^2$.

As the ligand which contains a monocyclic aromatic ring formed by at least one combination of $R^3$ and $R^4$, $R^4$ and $R^5$, or $R^5$ and $R^6$, as mentioned above, and is coordinated to M, there can be mentioned the following ones.

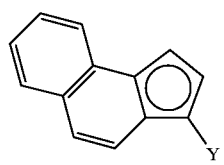
(1)

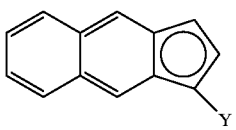
(2)

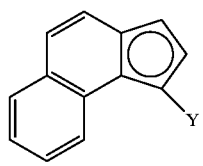
(3)

Of these, preferred is the ligand represented by the formula (1).

The aromatic ring mentioned above may be substituted with a halogen atom, a hydrocarbon group of 1 to 20 carbon atoms or a halogenated hydrocarbon group of 1 to 20 carbon atoms.

Examples of the halogen atoms, the hydrocarbon groups of 1 to 20 carbon atoms and the halogenated hydrocarbon groups of 1 to 20 carbon atoms for substituting the aromatic ring are those described for $R^1$ and $R^2$.

$X^1$ and $X^2$ are each independently hydrogen, a halogen atom, a hydrocarbon group of 1 to 20 carbon atoms, a halogenated hydrocarbon group of 1 to 20 carbon atoms, an oxygen-containing group or a sulfur-containing group.

Examples of the halogen atoms, the hydrocarbon groups of 1 to 20 carbon atoms, the halogenated hydrocarbon groups of 1 to 20 carbon atoms and the oxygen-containing groups are those described for $R^1$ and $R^2$.

Examples of the sulfur-containing groups include those described for $R^1$ and $R^2$; and further sulfonato groups, such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzenesulfonato; and sulfinato groups, such as methylsulfinato, phenylsulfinato, benzylsulfinato, p-toluenesulfinato, trimethylbenzenesulfinato and pentafluorobenzenesulfinato.

Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^7$—, —P(R$^7$)—, —P(O) (R$^7$)—, —BR$^7$— or —AlR$^7$—, where $R^7$ is hydrogen, a halogen atom, a hydrocarbon group of 1 to 20 carbon atoms or a halogenated hydrocarbon group of 1 to 20 carbon atoms. Examples of the divalent hydrocarbon groups of 1 to 20 carbon atoms include alkylene groups, such as methylene, dimethylmethylene, 1,2-ethylene, dimethyl-1,2-ethylene, 1,3-trimethylene, 1,4-tetramethylene, 1,2-cyclohexylene and 1,4-cyclohexylene, and arylalkylene groups, such as diphenylmethylene and diphenyl-1,2-ethylene.

Examples of the divalent halogenated hydrocarbon groups include the above-mentioned divalent hydrocarbon groups of 1 to 20 carbon atoms, which are halogenated, such as chloromethylene.

Examples of the divalent silicon-containing groups include alkylsilylene, alkylarylsilylene and arylsilylene groups, such as methylsilylene, dimethylsilylene, diethylsilylene, di(n-propyl)silylene, di(i-propyl) silylene, di(cyclohexyl)silylene, methylphenylsilylene, diphenylsilylene, di(p-tolyl)silylene and di(p-chlorophenyl) silylene; and alkyldisilylene, alkylaryldisilylene and aryldisilylene groups, such as tetramethyl-1,2-disilylene and tetraphenyl-1,2-disilylene.

Examples of the divalent germanium-containing groups include those wherein silicon is replaced with germanium in the above-mentioned divalent silicon-containing groups.

Examples of the divalent tin-containing groups include those wherein silicon is replaced with tin in the above-mentioned divalent silicon-containing groups.

$R^7$ is a halogen atom, a hydrocarbon group of 1 to 20 carbon atoms or a halogenated hydrocarbon group of 1 to 20 carbon atoms, examples of which are those described for $R^1$ and $R^2$.

Of the above groups, preferred are divalent silicon-containing groups, divalent germanium-containing groups and divalent tin-containing group, and more preferred are divalent silicon-containing groups. Of these, particularly preferred are alkylsilylene, alkylarylsilylene and arylsilylene.

Listed below are examples of the transition metal compounds represented by the formula (B).

| $R^1$ | $R^2$ | $R^5$ | $R^6$ | $R^8$ | $R^9$ | $R^{10}$ | $R^{11}$ | Y | $X^1$ | $X^2$ | M |
|---|---|---|---|---|---|---|---|---|---|---|---|
| H | H | H | H | H | H | H | H | SiMe$_2$ | Cl | Cl | Zr |
| CH$_3$ | H | H | H | H | H | H | H | SiMe$_2$ | Cl | Cl | Zr |
| CH$_3$ | H | H | H | H | H | H | H | SiMePh | Cl | Cl | Zr |
| CH$_3$ | H | H | H | H | H | H | H | SiPh$_2$ | Cl | Cl | Zr |
| CH$_3$ | H | H | H | H | H | H | H | Si(p-tolyl)$_2$ | Cl | Cl | Zr |
| CH$_3$ | H | H | H | H | H | H | H | Si(pClPh)$_2$ | Cl | Cl | Zr |
| CH$_3$ | H | H | H | H | H | H | H | C$_2$H$_5$ | Cl | Cl | Zr |
| CH$_3$ | H | H | H | H | H | H | H | GeMe$_2$ | Cl | Cl | Zr |
| CH$_3$ | H | H | H | H | H | H | H | SnMe$_2$ | Cl | Cl | Zr |
| CH$_3$ | H | H | H | H | H | H | H | SiMe$_2$ | Br | Br | Zr |
| CH$_3$ | H | H | H | H | H | H | H | SiMe$_2$ | Cl | OSO$_2$CH$_3$ | Zr |
| CH$_3$ | H | H | H | H | H | H | H | SiMe$_2$ | Cl | SO$_2$CH$_3$ | Zr |
| CH$_3$ | H | H | H | H | H | H | H | SiMe$_2$ | Cl | Cl | Ti |
| CH$_3$ | H | H | H | H | H | H | H | SiMe$_2$ | Cl | Cl | Hf |
| C$_2$H$_5$ | H | H | H | H | H | H | H | SiMe$_2$ | Cl | Cl | Zr |
| nC$_3$H$_7$ | H | H | H | H | H | H | H | SiMe$_2$ | Cl | Cl | Zr |
| C$_6$H$_{13}$ | H | H | H | H | H | H | H | SiMe$_2$ | Cl | Cl | Zr |
| CH$_3$ | CH$_3$ | H | H | H | H | H | H | SiMe$_2$ | Cl | Cl | Zr |
| CH$_3$ | CH$_3$ | H | H | H | H | H | H | SiPh$_2$ | Cl | Cl | Zr |
| CH$_3$ | CH$_3$ | CH$_3$ | H | H | H | H | H | SiMe$_2$ | Cl | Cl | Zr |
| CH$_3$ | H | Cl | H | H | H | H | H | SiMe$_2$ | Cl | Cl | Zr |
| CH$_3$ | H | CH$_3$ | H | H | H | H | H | SiMe$_2$ | Cl | Cl | Zr |
| CH$_3$ | H | C$_2$H$_5$ | H | H | H | H | H | SiMe$_2$ | Cl | Cl | Zr |
| CH$_3$ | H | C$_6$H$_{13}$ | H | H | H | H | H | SiMe$_2$ | Cl | Cl | Zr |
| CH$_3$ | H | H | CH$_3$ | H | H | H | H | SiMe$_2$ | Cl | Cl | Zr |
| CH$_3$ | H | CH$_3$ | CH$_3$ | H | H | H | H | SiMe$_2$ | Cl | Cl | Zr |
| CH$_3$ | H | CH$_2$*$^1$ | CH$_3$ | H | H | H | CH$_2$*$^1$ | SiMe$_2$ | Cl | Cl | Zr |

-continued

| | | | | | | | | | | | |
|---|---|---|---|---|---|---|---|---|---|---|---|
| CH$_3$ | H | H | H | H | H | H | C$_6$H$_{13}$ | SiMe$_2$ | Cl | Cl | Zr |

*1: R$^5$ and R$^{11}$ are bonded to each other to form a five-membered ring.
Me: metyl; Et: ethyl; Ph: phenyl.

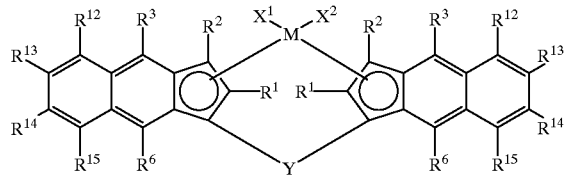

| R$^1$ | R$^2$ | R$^3$ | R$^6$ | R$^{12}$ | R$^{13}$ | R$^{14}$ | R$^{15}$ | Y | X$^1$ | X$^2$ | M |
|---|---|---|---|---|---|---|---|---|---|---|---|
| H | H | H | H | H | H | H | H | SiMe$_2$ | Cl | Cl | Zr |
| CH$_3$ | H | H | H | H | H | H | H | SiMe$_2$ | Cl | Cl | Zr |
| CH$_3$ | H | H | H | H | H | H | H | SiPh$_2$ | Cl | Cl | Zr |
| CH$_3$ | CH$_3$ | H | H | H | H | H | H | SiMe$_2$ | Cl | Cl | Zr |
| CH$_3$ | H | CH$_3$ | H | H | H | H | H | SiMe$_2$ | Cl | Cl | Zr |
| CH$_3$ | H | CH$_3$ | CH$_3$ | H | H | H | H | SiMe$_2$ | Cl | Cl | Zr |
| CH$_3$ | H | CH$_2$*2 | CH$_2$*2 | CH$_2$*2 | H | H | CH$_2$*2 | SiMe$_2$ | Cl | Cl | Zr |
| CH$_3$ | H | CH$_3$ | CH$_3$ | CH$_3$ | H | H | CH$_3$ | SiMe$_2$ | Cl | Cl | Zr |

*2: R$^3$ and R$^{12}$, and R$^6$ and R$^{15}$ are bonded to each other to form a five-memebered ring, respectively.
Me: methyl; Ph: phenyl

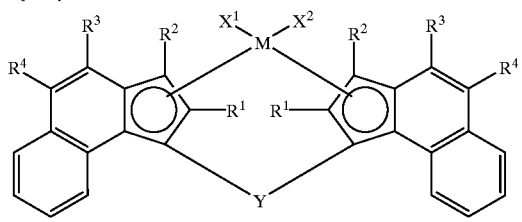

| R$^1$ | R$^2$ | R$^3$ | R$^4$ | Y | X$^1$ | X$^2$ | M |
|---|---|---|---|---|---|---|---|
| H | H | H | H | SiMe$_2$ | Cl | Cl | Zr |
| H | CH$_3$ | H | H | SiMe$_2$ | Cl | Cl | Zr |
| H | CH$_3$ | H | CH$_3$ | SiMe$_2$ | Cl | Cl | Zr |
| H | CH$_3$ | CH$_3$ | CH$_3$ | SiMe$_2$ | Cl | Cl | Zr |
| CH$_3$ | CH$_3$ | H | H | SiMe$_2$ | Cl | Cl | Zr |
| CH$_3$ | CH$_3$ | H | CH$_3$ | SiMe$_2$ | Cl | Cl | Zr |
| CH$_3$ | CH$_3$ | CH$_3$ | CH$_3$ | SiMe$_2$ | Cl | Cl | Zr |

Me: metyl.

Also employable in the invention are transition metal compounds wherein zirconium is replaced with titanium or hafnium in the above-mentioned compounds.

The transition metal compounds mentioned above are used generally in the form of racemic modification as the olefin polymerization catalyst component, but they can be used also in the form of R type or S type.

The indene derivative ligands for the transition metal compounds can be synthesized in accordance with ordinary organic synthesis through, for example, the reaction route described below.

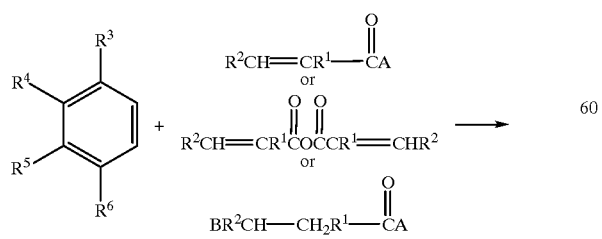

-continued

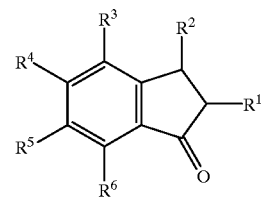

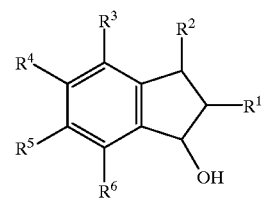

-continued

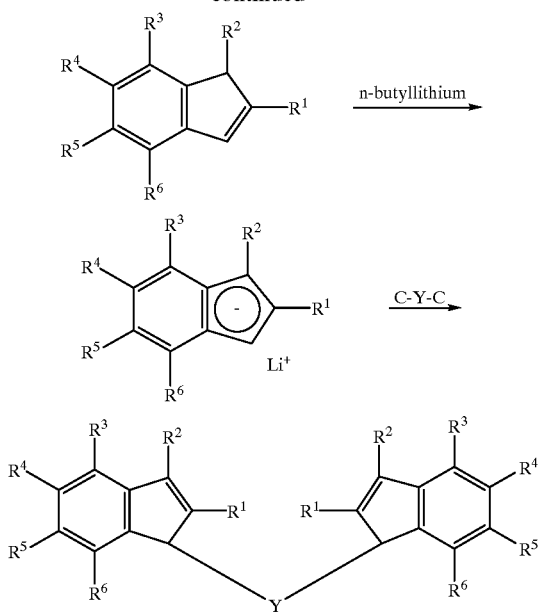

wherein A, B, C are each halogen.

The transition metal compounds used in the invention can be synthesized from these indene derivatives in accordance with conventionally known processes, for example, described in Japanese Patent Laid-Open Publication No. 268307/1992.

In the present invention, a transition metal compound (metallocene compound) represented by the following formula (C) is also employable.

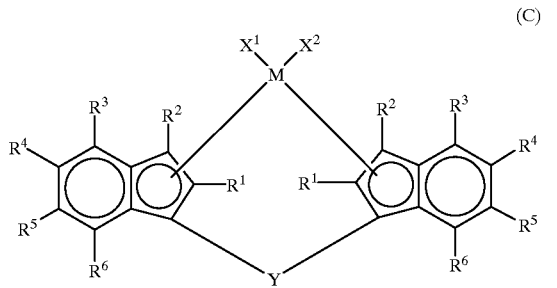

(C)

In the formula (C), M, $R^1$, $R^2$, $R^3$, $R^4$, $R^5$ and $R^6$ have the same meanings described for those in the aforesaid formula (B).

Of $R^3$, $R^4$, $R^5$ and $R^6$, at least two groups including $R^3$ are preferably alkyl groups, and it is more preferred that $R^3$ and $R^5$, or $R^3$ and $R^6$ are alkyl groups. These alkyl groups are preferably secondary or tertiary alkyl groups, and may be substituted with halogen atoms or silicon-containing groups. As the halogen atoms and the silicon-containing groups, there can be mentioned those substituents as described for $R^1$ and $R^2$.

Of the groups $R^3$, $R^4$, $R^5$ and $R^6$, other groups than the alkyl groups are each preferably hydrogen.

Examples of the hydrocarbon groups of 1 to 20 carbon atoms include straight chain and branched chain alkyl groups and cyclic alkyl groups, such as methyl, ethyl, n-propyl, i-propyl, n-butyl, i-butyl, sec-butyl, tert-butyl, pentyl, hexyl, cyclohexyl, heptyl, octyl, nonyl, dodecyl, eicosyl, norbornyl and adamantyl; and arylalkyl groups, such as benzyl, phenylethyl, phenylpropyl and tolylmethyl.

These groups may contain a double bond or a triple bond.

Two groups selected from $R^3$, $R^4$, $R^5$ and $R^6$ may be bonded to each other to form a monocyclic or polycyclic hydrocarbon ring other than the aromatic ring.

Examples of the halogen atoms are those described for $R^1$ and $R^2$.

$X^1$, $X^2$, Y and $R^7$ have the same meanings described for those in the aforesaid formula (B).

Listed below are examples of the metallocene compounds (transition metal compounds) represented by the formula (C).

rac-Dimethylsilylene-bis(4,7-dimethyl-1-indenyl) zirconium dichloride, rac-Dimethylsilylene-bis(2,4,7-trimethyl-1-indenyl) zirconium dichloride, rac-Dimethylsilylene-bis(2,4,6-trimethyl-1-indenyl) zirconium dichloride, rac-Dimethylsilylene-bis(2,5,6-trimethyl-1-indenyl) zirconium dichloride, rac-Dimethylsilylene-bis(2,4,5,6-tetramethyl-1-indenyl) zirconium dichloride, rac-Dimethylsilylene-bis(2,4,5,6,7-pentamethyl-1-indenyl)zirconium dichloride, rac-Dimethylsilylene-bis(2-methyl-4-n-propyl-7-methyl-1-indenyl)zirconium dichloride, rac-Dimethylsilylene-bis(4-i-propyl-7-methyl-1-indenyl) zirconium dichloride, rac-Dimethylsilylene-bis(2-methyl-4-i-propyl-7-methyl-1-indenyl)zirconium dichloride, rac-Dimethylsilylene-bis(2-methyl-4-i-propyl-6-methyl-1-indenyl)zirconium dichloride, rac-Dimethylsilylene-bis(2-methyl-4-methyl-6-i-propyl-1-indenyl)zirconium dichloride, rac-Dimethylsilylene-bis(2-methyl-4-i-propyl-5-methyl-1-indenyl)zirconium dichloride, rac-Dimethylsilylene-bis(2-methyl-4,6-di(i-propyl)-1-indenyl)zirconium dichloride, rac-Dimethylsilylene-bis(2-methyl-4 6-di(i-propyl)-7-methyl-1-indenyl)zirconium dichloride, rac-Dimethylsilylene-bis (2-methyl-4-i-butyl-7-methyl-1-indenyl)zirconium dichloride, rac-Dimethylsilylene-bis(2-methyl-4-sec-butyl-7-methyl-1-indenyl)zirconium dichloride, rac-Dimethylsilylene-bis(2-methyl-4,6-di (sec-butyl)-1-indenyl)zirconium dichloride, rac-Dimethylsilylene-bis(2-methyl-4-tert-butyl-7-methyl-1-indenyl)zirconium dichloride, rac-Dimethylsilylene-bis(2-methyl-4-cyclohexyl-7-methyl-1-indenyl)zirconium dichloride, rac-Dimethylsilylene-bis(2-methyl-4-benzyl-7-methyl-1-indenyl)zirconium dichloride, rac-Dimethylsilylene-bis(2-methyl-4-phenylethyl-7-methyl-1-indenyl)zirconium dichloride, rac-Dimethylsilylene-bis(2-methyl-4-phenyldichloromethyl-7-methyl-1-inderyl)zirconium dichloride, rac-Dimethylsilylene-bis(2-methyl-4-chloromethyl-7-methyl-1-indenyl)zirconium dichloride, rac-Dimethylsilylene-bis(2-methyl-4-trimethylsilylmethyl-7-methyl-1-indenyl)zirconium dichloride, rac-Dimethylsilylene-bis(2-methyl-4-trimethylsiloxymethyl-7-methyl-1-indenyl)zirconium dichloride, rac-Diethylsilylene-bis(2-methyl-4-i-propyl-7-methyl-1-indenyl)zirconium dichloride, rac-Di(i-propyl)silylene-bis(2-methyl-4-i-propyl-7-methyl-i-indenyl)zirconium dichloride, rac-Di(n-butyl)silylene-bis(2-methyl-4-i-propyl-7-methyl-1-indenyl)zirconium dichloride, rac-Di(cyclohexyl)silylene-bis(2-methyl-4-i-propyl-7-methyl-1-indenyl)zirconium dichloride, rac-Methylphenylsilylene-bis(2-methyl-4-i-propyl-7-methyl-1-indenyl)zirconium dichloride, rac-Diphenylsilylene-bis(2-methyl-4-i-propyl-7-methyl-1-indenyl)zirconium dichloride, rac-Diphenylsilylene-bis(2-methyl-4-di(i-propyl)-1-indenyl)zirconium dichloride, rac-Di(p-tolyl)silylene-bis(2-methyl-4-i-propyl-7-methyl-1-indenyl)zirconium dichloride, rac-Di(p-chlorophenyl)silylene-bis(2-methyl-4-i-propyl-7-methyl-1-indenyl)zirconium dichloride, rac-Dimethylsilylene-bis(2-methyl-4-i-propyl-7-methyl-1-indenyl) zirconium dibromide, rac-Dimethylsilylene-bis(2-methyl-4-i-propyl-7-methyl-1-indenyl)zirconium dimethyl, rac-Dimethylsilylene-bis(2-methyl-4-i-propyl-7-methyl-1-indenyl)zirconium methylchloride, rac-Dimethylsilylene-bis(2-methyl-4-i-propyl-7-methyl-1-indenyl)zirconium-bis(methanesulfonato)

rac-Dimethylsilylene-bis(2-methyl-4-i-propyl-7-methyl-1-indenyl)zirconium-bis(p-phenylsulfinato), rac-Dimethylsilylene-bis(2-methyl-3-methyl-4-i-propyl-6-methyl-1-indenyl)zirconium dichloride, rac-Dimethylsilylene-bis(2-ethyl-4-i-propyl-6-methyl-1-indenyl)zirconium dichloride, and rac-Dimethylsilylene-bis(2-phenyl-4-i-propyl-6-methyl-1-indenyl)zirconium dichloride.

Also employable in the invention are transition metal compounds wherein zirconium is replaced with titanium metal or hafnium metal in the above-mentioned compounds.

The transition metal compounds mentioned above are used generally in the form of racemic modification, but they can be used also in the form of R type or S type.

The indene derivative ligands for the transition metal compounds can be synthesized in accordance with ordinary organic synthesis through, for example, the aforementioned reaction route.

The transition metal compounds (metallocene compounds) represented by the formula (C) can be synthesized from these indene derivatives in accordance with conventionally known processes, for example, described in Japanese Patent Laid-Open Publication No. 268307/1992.

In the present invention, a transition metal compound (metallocene compound) represented by the following formula (D) is also employable.

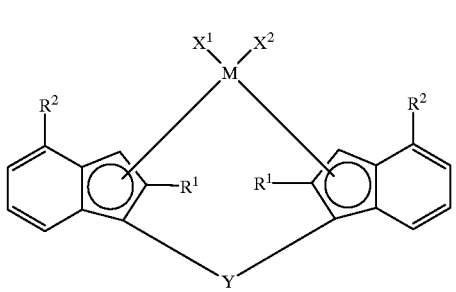

In the formula (D), M, $R^1$, $X^1$, $X^2$ and Y have the same meanings as described for those in the aforesaid formula (B) or (C).

$R^1$ is preferably a hydrocarbon group, more preferably a hydrocarbon group of 1 to 4 carbon atoms, e.g., methyl, ethyl, propyl and butyl.

$X^1$ and $X^2$ are each preferably a halogen atom or a hydrocarbon group of 1 to 20 carbon atoms.

$R^2$ is an aryl group of 6 to 16 carbon atoms, for example, phenyl, α-naphthyl, β-naphthyl, anthracenyl, phenanthryl, pyrenyl, acenaphthyl, perinaphthenyl or aceanthrylenyl. Of these, phenyl or naphthyl is preferred. These aryl groups may be substituted with halogen atoms, hydrocarbon groups of 1 to 20 carbon atoms or halogenated hydrocarbon groups of 1 to 20 carbon atoms such as described for $R^1$.

Listed below are examples of the transition metal compounds (metallocene compounds) represented by the formula (D).

rac-Dimethylsilylene-bis(4-phenyl-1-indenyl)zirconium dichloride, rac-Dimethylsilylene-bis(2-methyl-4-phenyl-1-indenyl)zirconium dichloride, rac-Dimethylsilylene-bis(2-methyl-4-(α-naphthyl)-1-indenyl)zirconium dichloride, rac-Dimethylsilylene-bis(2-methyl-4-(β-naphthyl)-1-indenyl)zirconium dichloride, rac-Dimethylsilylene-bis(2-methyl-4-(1-anthracenyl)-1-indenyl)zirconium dichloride, rac-Dimethylsilylene-bis(2-methyl-4-(2-anthracenyl)-1-indenyl)zirconium dichloride, rac-Dimethylsilylene-bis(2-methyl-4-(9-anthracenyl)-1-indenyl)zirconium dichloride, rac-Dimethylsilylene-bis(2-methyl-4-(9-phenanthryl)-1-indenyl)zirconium dichloride, rac-Dimethylsilylene-bis(2-methyl-4-(p-fluorophenyl)-1-indenyl)zirconium dichloride, rac-Dimethylsilylene-bis(2-methyl-4-(pentafluorophenyl)-1-indenyl)zirconium dichloride, rac-Dimethylsilylene-bis(2-methyl-4-(p-chlorophenyl)-1-indenyl)zirconium dichloride, rac-Dimethylsilylene-bis(2-methyl-4-(m-chlorophenyl)-1-indenyl)zirconium dichloride, rac-Dimethylsilylene-bis(2-methyl-4-(p-chlorophenyl)-1-indenyl)zirconium dichloride, rac-Dimethylsilylene-bis(2-methyl-4-(o,p-dichlorophenyl)phenyl-1-indenyl)zirconium dichloride, rac-Dimethylsilylene-bis(2-methyl-4-(p-bromophenyl)-1-indenyl)zirconium dichloride, rac-Dimethylsilylene-bis(2-methyl-4-(p-tolyl)-1-indenyl)zirconium dichloride,
rac-Dimethylsilylene-bis(2-methyl-4-(m-tolyl)-1-indenyl)zirconium dichloride,
rac-Dimethylsilylene-bis(2-methyl-4-(o-tolyl)-1-indenyl)zirconium dichloride,
rac-Dimethylsilylene-bis(2-methyl-4-(o,o'-dimethylphenyl)-1-indenyl)zirconium dichloride,
rac-Dimethylsilylene-bis(2-methyl-4-(p-ethylphenyl)-1-indenyl)zirconium dichloride,
rac-Dimethylsilylene-bis(2-methyl-4-(p-i-propylphenyl)-1-indenyl)zirconium dichloride,
rac-Dimethylsilylene-bis(2-methyl-4-(p-benzylphenyl)-1-indenyl)zirconium dichloride,
rac-Dimethylsilylene-bis(2-methyl-4-(p-biphenyl)-1-indenyl)zirconium dichloride,
rac-Dimethylsilylene-bis(2-methyl-4-(m-biphenyl)-1-indenyl)zirconium dichloride,
rac-Dimethylsilylene-bis(2-methyl-4-(p-trimethylsilylphenyl)-1-indenyl)zirconium dichloride,
rac-Dimethylsilylene-bis(2-methyl-4-(m-trimethylsilylphenyl)-1-indenyl)zirconium dichloride,
rac-Dimethylsilylene-bis(2-ethyl-4-phenyl-1-indenyl)zirconium dichloride,
rac-Diphenylsilylene-bis(2-ethyl-4-phenyl-1-indenyl)zirconium dichloride,
rac-Dimethylsilylene-bis(2-phenyl-4-phenyl-1-indenyl)zirconium dichloride,
rac-Dimethylsilylene-bis(2-n-propyl-4-phenyl-1-indenyl)zirconium dichloride,
rac-Diethylsilylene-bis(2-methyl-4-phenyl-1-indenyl)zirconium dichloride,
rac-Di-(i-propyl)silylene-bis(2-methyl-4-phenyl-1-indenyl)zirconium dichloride,
rac-Di-(n-butyl)silylene-bis(2-methyl-4-phenyl-1-indenyl)zirconium dichloride,
rac-Dicyclohexylsilylene-bis(2-methyl-4-phenyl-1-indenyl)zirconium dichloride,
rac-Methylphenylsilylene-bis(2-methyl-4-phenyl-1-indenyl)zirconium dichloride,
rac-Diphenylsilylene-bis(2-methyl-4-phenyl-1-indenyl)zirconium dichloride,
rac-Di(p-tolyl)silylene-bis(2-methyl-4-phenyl-1-indenyl)zirconium dichloride,
rac-Di(p-chlorophenyl)silylene-bis(2-methyl-4-phenyl-1-indenyl)zirconium dichloride,
rac-Methylene-bis(2-methyl-4-phenyl-1-indenyl)zirconium dichloride,
rac-Ethylene-bis(2-methyl-4-phenyl-1-indenyl)zirconium dichloride,
rac-Dimethylgermylene-bis(2-methyl-4-phenyl-1-indenyl)zirconium dichloride,
rac-Dimethylstannylene-bis(2-methyl-4-phenyl-1-indenyl)zirconium dichloride,
rac-Dimethylsilylene-bis(2-methyl-4-phenyl-1-indenyl)zirconium dibromide,
rac-Dimethylsilylene-bis(2-methyl-4-phenyl-1-indenyl)zirconium dimethyl,
rac-Dimethylsilylene-bis(2-methyl-4-phenyl-1-indenyl)zirconium methylchloride,
rac-Dimethylsilylene-bis(2-methyl-4-phenyl-1-indenyl)zirconium chloride $SO_2Me$, and
rac-Dimethylsilylene-bis(2-methyl-4-phenyl-1-indenyl)zirconium chloride $OSO_2Me$.

Also employable in the invention are transition metal compounds wherein zirconium is replaced with titanium metal or hafnium metal in the above-mentioned compounds.

The transition metal compounds represented by the formula (D) can be prepared in accordance with "Journal of Organometallic Chem.", 288(1985), pp. 63–67, and European Patent Publication No. 0,320,762 (specification and examples), for example, in the following manner.

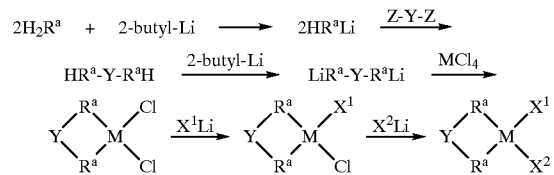

wherein Z is Cl, Br, I or o-tosyl, and $H_2R^a$ is

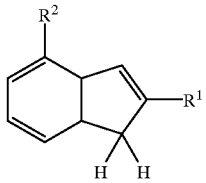

The transition metal compounds (D) are used generally in the form of racemic modification, but they can be used also in the form of R type or S type.

In the present invention, a compound represented by the following formula (E-1) can be also employed as the metallocene compound.

$$L^a MX_2 \qquad (E-1)$$

wherein, M is a metal of Group IV of the periodic table or a metal of lanthanide series;

$L^a$ is a derivative of delocalization π bond group and imparts restraint geometrical shape to the metal M active site; and the X's are each independently hydrogen, halogen, a hydrocarbon group of 20 or less carbon, silicon or germanium atoms, a silyl group or a germyl group.

Of the compounds of the formula (E-1), preferred are compounds represented by the following formula (E-2).

wherein M is titanium, zirconium or hafnium; X is the same as described above;

Cp is a substituted cyclopentadienyl group which is π-bonded to M and has a substituent Z;

Z is oxygen, sulfur, boron or an element of Group IVA of the periodic table;

Y is a ligand containing nitrogen, phosphorus, oxygen or sulfur; and

Z and Y may together form a condensed ring.

Listed below are examples of the compounds represented by the formula (E-2).

(Dimethyl(t-butylamide)(tetramethyl-η⁵-cyclopentadienyl)silane)titanium dichloride, ((t-Butylamide)(tetramethyl-η⁵-cyclopentadienyl)-1,2-ethanediyl)titanium dichloride, (Dibenzyl(t-butylamide)(tetramethyl-η5-cyclopentadienyl)silane)titanium dichloride, (Dimethyl(t-butylamide)(tetramethyl-η⁵-cyclopentadienyl)silane)dibenzyltitanium, (Dimethyl(t-butylamide)(tetramethyl-η⁵-cyclopentadienyl)silane)dimethyltitanium, ((t-Butylamide) (tetramethyl-η⁵-cyclopentadienyl)-1,2-ethanediyl)dibenzyltitanium, ((Methylamide) (tetramethyl-η⁵-cyclopentadienyl)-1,2-ethanediyl)dineopentyltitanium, ((Phenylphosphide)(tetramethyl-η⁵-cyclopentadienyl)-methylene)diphenyltitanium, (Dibenzyl(t-butylamide)(tetramethyl-η⁵-cyclopentadienyl)silane)dibenzyltitanium, (Dimethyl (benzylamide) (η⁵-cyclopentadienyl) silane) di(trimethylsilyl)titanium, (Dimethyl(phenylphosphide)-(tetramethylη⁵-cyclopentadienyl)silane)dibenzyltitanium, (Tetramethyl-η⁵-cyclopentadienyl)-1,2-ethanediyl) dibenzyltitanium, (2-η⁵-(Tetramethyl-cyclopentadienyl)-1-methyl-ethanolate(2-))dibenzyltitanium, (2 -η⁵- (Tetramethyl-cyclopentadienyl)-1-methyl-ethanolate(2-))dimethyltitanium, (2-((4a,4b,8a,9,9a-η)-9H-fluorene-9-yl)cyclohexanolate (2-))dimethyltitanium, and (2-((4a,4b,8a,9,9a-η)-9H-fluorene-9-yl)cyclohexanolate (2-))dibenzyltitanium.

In the present invention, the metallocene compounds mentioned above can be used in combination of two or more kinds.

Some examples of titanium compounds are mentioned above as the metallocene compounds, but compounds wherein titanium is replaced with zirconium or hafnium in the above-mentioned titanium compounds can be also exemplified.

Those compounds may be used alone or in combination of two or more kinds.

As the metallocene compounds (E-1) and (E-2), zirconocene compounds which have zirconium as the central metal atom and have at least two ligands containing a cyclopentadienyl skeleton. In the metallocene compounds [VI], the central metal atom is preferably titanium.

The metallocene compounds may be used by diluting with hydrocarbons or halogenated hydrocarbons.

The metallocene compounds may be used by contacting with the particulate carrier compounds.

As the carrier compounds, there can be used inorganic carrier compounds such as $SiO_2$, $Al_2O_3$, $B_2O_3$, MgO, $ZrO_2$, CaO, $TiO_2$, ZnO, $Zn_2O$, $SnO_2$, BaO and ThO; and resins such as polyethylene, polypropylene, poly-1-butene, poly-4-methyl-1-pentene and styrene-divinylbenzene copolymer. These carrier compounds may be used in combination of two or more kinds.

Next, the organoaluminum oxy-compound and the ionizable ionic compound used for forming the catalyst (b) (catalyst comprising a metallocene compound of a transition metal selected from elements of Group IV of the periodic table, and an organoaluminum oxy compound or an ionizable ionic compound) are described.

The organoaluminum oxy-compound used in the invention may be either aluminoxane conventionally known or a benzene-insoluble organoaluminum oxy-compound.

The conventionally known aluminoxane is represented by the following formula (1) or (2).

(1)

(2)

wherein R is a hydrocarbon group such as methyl, ethyl, propyl and butyl, preferably methyl or ethyl, particularly preferably methyl, and m is an integer of not less than 2, preferably an integer of 5 to 40.

This aluminoxane may be formed from mixed alkyloxyaluminum units consisting of alkyloxyaluminum units represented by the formula $(OAl(R^1))$ and alkyloxyaluminum units represented by the formula $(OAl(R^2))$ (in these formulas, $R^1$ and $R^2$ are each the same hydrocarbon group as described for R, and $R^1$ and $R^2$ are different from each other).

The conventionally known aluminoxane can be prepared by, for example, the following procedures, and the aluminoxane is generally recovered in the form of an aromatic hydrocarbon solvent solution.

(1) An organoaluminum compound such as trialkylaluminum is added to a hydrocarbon solvent suspension of compounds containing adsorbed water or salts containing water of crystallization, e.g., magnesium chloride hydrate, copper sulfate hydrate, aluminum sulfate hydrate, nickel sulfate hydrate and cerous chloride hydrate, so as to allow the organoaluminum compound to react with the adsorbed water or the water of crystallization, and the reaction product is recovered as an aromatic hydrocarbon solvent solution.

(2) Water, ice or water vapor is allowed to directly act on an organoaluminum compound such as trialkylaluminum in a medium such as benzene, toluene, ethyl ether or tetrahydrofuran, and the reaction product is recovered as an aromatic hydrocarbon solvent solution.

Of the above procedures, the procedure (1) is preferably used.

Examples of the organoaluminum compounds used for preparing the solution of aluminoxane include the aforesaid organoaluminum compounds. More specifically, there can be mentioned:

trialkylaluminums, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum, tridecylaluminum, tricyclohexylaluminum and tricyclooctylaluminum;

alkenylaluminums represented by the formula $(i-C_4H_9)_xAl_y(C_5H_{10})_z$ (x, y and z are each a positive number, and $z \geq 2x$), such as isoprenylaluminum;

dialkylaluminum halides, such as dimethylaluminum chloride, diethylaluminum chloride, diethylaluminum bromide and diisobutylaluminum chloride;

dialkylaluminum hydrides, such as diethylaluminum hydride and diisobutylaluminum hydride;

dialkylaluminum alkoxides, such as dimethylaluminum methoxide and diethylaluminum ethoxide; and dialkylaluminum aryloxides, such as diethylaluminum phenoxide.

Of these, preferred are trialkylaluminums.

The organoaluminum compounds mentioned above are used singly or in combination.

The benzene-insoluble organoaluminum oxy-compound used in the invention can be obtained by, for example, contacting the solution of aluminoxane with water or an active hydrogen-containing compound or contacting the organoaluminum compound with water.

In the benzene-insoluble organoaluminum oxy-compound used for the invention, a ratio of the absorbance at about 1,260 cm$^{-1}$ ($D_{1260}$) to the absorbance at about 1,220 cm$^{-1}$ ($D_{1220}$) obtained by the infrared spectroscopic analysis of the compound, ($D_{1260}/D_{1220}$), is not more than 0.09, preferably not more than 0.08, particularly preferably in the range of 0.04 to 0.07.

The benzene-insoluble organoaluminum oxy-compound is presumed to have alkyloxyaluminum units represented by the following formula:

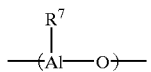

wherein $R^7$ is a hydrocarbon group of 1 to 12 carbon atoms. Examples of such hydrocarbon groups include methyl, ethyl, n-propyl, isopropyl, n-butyl, isobutyl, pentyl, hexyl, octyl, decyl, cyclohexyl and cyclooctyl. Of these, preferred are methyl and ethyl, and particularly preferred is methyl.

This benzene-insoluble organoaluminum oxy-compound may have, in addition to the alkyloxyaluminum units represented by the above formula, oxyaluminum units represented by the following formula:

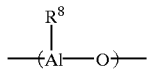

wherein $R^8$ is a hydrocarbon group of 1 to 12 carbon atoms, an alkoxy group of 1 to 12 carbon atoms, an aryloxy group of 6 to 20 carbon atoms, a hydroxyl group, halogen or hydrogen.

$R^8$ is different from $R^7$ in the aforesaid formula.

When the organoaluminum oxy-compound contains the oxyaluminum units, it is desired that the alkyloxyaluminum units are contained in an amount of not less than 30% by mol, preferably not less than 50% by mol, particularly preferably not less than 70% by mol.

The organoaluminum oxy-compound used in the invention may contain a small amount of an organic compound component of other metal than aluminum.

The ionizable ionic compound used in the present invention includes Lewis acids, ionic compounds, borane compounds and carborane compounds.

The Lewis acids include, for example, a compound represented by the formula: $BR_3$ wherein each R is independently a phenyl group which may have substituents such as fluorine, methyl and trifluoromethyl, or a fluorine atom.

Examples of the compounds represented by the above formula include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris (3,5-dimethylphenyl)boron.

Examples of the ionic compounds include trialkyl-substituted ammonium salts, N,N-dialkylanilinium salts, dialkylammonium salts and triarylphosphonium salts.

Particular examples of the trialkyl-substituted ammonium salts include:

triethylammoniumtetra(phenyl)boron, tripropylammoniumtetra(phenyl)boron, tri(n-butyl)ammoniumtetra(phenyl)boron, trimethylammoniumtetra(p-tolyl)boron, trimethylammoniumtetra(o-tolyl)boron, tributylammoniumtetra(pentafluorophenyl)boron, tripropylammoniumtetra(o,p-dimethylphenyl)boron, tributylammoniumtetra(m,m-dimethylphenyl)boron, tributylammoniumtetra(p-trifluoromethylphenyl)boron, and tri(n-butyl)ammoniumtetra(o-tolyl)boron.

Particular examples of the N,N,-dialkylanilinium salts include:

N,N-dimethylaniliniumtetra(phenyl)boron,

N,N-diethylaniliniumtetra(phenyl)boron, and

N,N-2,4,6-pentamethylaniliniumtetra(phenyl)boron.

Particular examples of the dialkylammonium salts include:

di(1-propyl)ammnoniumtetra(pentafluorophenyl)boron, and dicyclohexylammoniumtetra(phenyl)boron.

Also employable as the ionic compound are triphenylcarbeniumtetrakis(pentafluorophenyl)borate, N,N-dimethylaniliniumtetrakis(pentafluorophenyl)borate and ferroceniumtetra(pentafluorophenyl)borate.

Further, also employable as the borane compound are the following compounds:

decaborane (14);

salts of anion, such as bis(tri(n-butyl)ammonium)nonaborate, bis(tri(n-butyl)ammonium)decaborate, bis(tri(n-butyl)ammonium)undecaborate, bis(tri(n-butyl)ammonium)dodecaborate, bis(tri(n-butyl)ammonium)decachlorodecaborate, and bis(tri(n-butyl)ammonium)dodecachlorododecaborate; and salts of metallic borane anion, such as tri(n-butyl)ammonium-bis(dodecahydridedodecaborate) cobaltate(III), and bis(tri(n-butyl)ammonium)-bis (dodecahydridedodecaborate)nickelate(III).

Further, particular examples of carborane compounds include:

salts of anion, such as 4-carbanonaborane(14), 1,3-dicarbanonaborane(13), 6,9-dicarbadecaborane(14), dodecahydride-1-phenyl-1,3-dicarbanonaborane, dodecahydride-1-methyl-1,3-dicarbanonaborane, undecahydride-1,3-dimethyl-1,3-dicarbanonaborane, 7,8-dicarbaundecaborane(13), 2,7-dicarbaundecaborane(13), undecahydride-7,8-dimethyl-7,8-dicarbaundecaborane, dodecahydride-11-methyl-2,7-dicarbaundecaborane, tri(n-butyl)ammonium-1-carbadecaborate, tri(n-butyl)ammonium-1-carbaundecaborate,
tri(n-butyl)ammonium-1-carbadodecaborate,
tri(n-butyl)ammonium-1-trimethylsilyl-1-carbadecaborate,
tri(n-butyl)ammoniumbromo-1-carbadodecaborate,
tri(n-butyl)ammonium-6-carbadecaborate(14),
tri(n-butyl)ammonium-6-carbadecaborate(12),
tri(n-butyl)ammonium-7-carbaundecaborate(13),
tri(n-butyl)ammonium-7,8-dicarbaundecaborate(12),
tri(n-butyl)ammonium-2,9-dicarbaundecaborate(12),
tri(n-butyl)ammoniumdodecahydride-8-methyl-7,9-dicarbaundecaborate,
tri(n-butyl)ammoniumundecahydride-8-ethyl-7,9-dicarbaundecaborate,
tri(n-butyl)ammoniumundecahydride-8-butyl-7,9-dicarbaundecaborate,
tri(n-butyl)ammoniumundecahydride-8-allyl-7,9-dicarbaundecaborate,
tri(n-butyl)ammoniumundecahydride-9-trimethylsilyl-7,8-dicarbaundecaborate, and
tri(n-butyl)ammoniumundecahydride-4,6-dibromo-7-carbaundecaborate; and salts of metallic carborane anion, such as:
tri(n-butyl)ammoniumbis(nonahydride-1,3-dicarbanonaborate)cobaltate(III),
tri(n-butyl)ammoniumbis(undecahydride-7,8-dicarbaundecaborate)ferrate(III),
tri(n-butyl)ammoniumbis(undecahydride-7,8-dicarbaundecaborate)cobaltate(III),
tri(n-butyl)ammoniumbis(undecahydride-7,8-dicarbaundecaborate)nickelate(III),
tri(n-butyl)ammnoniumbis(undecahydride-7,8-dicarbaundecaborate)cuprate(III),
tri(n-butyl)ammoniumbis(undecahydride-7,8-dicarbaundecaborate)aurate(III),
tri(n-butyl)ammoniumbis(nonahydride-7,8-dimethyl-7,8-dicarbaundecaborate)ferrate(III),
tri(n-butyl)ammoniumbis(nonahydride-7,8-dimethyl-7,8-dicarbaundecaborate)chromate(III),
tri(n-butyl)ammoniumbis(tribromooctahydride-7,8-dicarbaundecaborate)cobaltate(III),
tris(tri(n-butyl)ammonium)bis(undecahydride-7-carbaundecaborate)chromate(III),
bis(tri(n-butyl)ammonium)bis(undecahydride-7-carbaundecaborate)manganate(IV),
bis(tri(n-butyl)ammonium)bis(undecahydride-7-carbaundecaborate)cobaltate(III), and
bis(tri(n-butyl)ammonium)bis(undecahydride-7-carbaundecaborate)nickelate(IV).

The ionizable ionic compounds mentioned above may be used in combination of two or more kinds.

In the present invention, the organoaluminum oxy-compound or the ionizable ionic compound may be used by supporting it on the aforementioned carrier compound.

For preparing the catalyst (b), the aforementioned organoaluminum compound may be used together with the organoaluminum oxy-compound or the ionizable ionic compound.

In the present invention, the ethylene (i), the α-olefin (ii) and the chain polyene group-containing norbornene compound (iii) are copolymerized in the presence of a catalyst [a] (catalyst comprising a soluble vanadium compound and a organoaluminum compound) or a catalyst [b] (catalyst comprising a metallocene compound of a transition metal selected from Group IV of the periodic table and an organoaluminum oxy-compound or an ionizable ionic compound), usually in a liquid phase. In this case, a hydrocarbon solvent is generally used, but an α-olefin such as propylene may be used as a solvent.

Examples of such hydrocarbon solvents include
aliphatic hydrocarbons, such as pentane, hexane, heptane, octane, decane, dodecane and kerosine, and halogenated derivatives of these aliphatic hydrocarbons;
alicyclic hydrocarbons, such as cyclohexane, methylcyclopentane and methylcyclohexane, and halogenated derivatives of these alicyclic hydrocarbons; and
aromatic hydrocarbons, such as benzene, toluene and xylene, and halogenated derivatives of these hydrocarbons, such as chlorobenzene. These solvents may be used in combination.

The copolymerization of ethylene (i), the α-olefin (ii) and the chain polyene group-containing norbornene compound (iii) may be carried out by any of batchwise and continuous processes. When the copolymerization is carried out continuously, the catalyst is used in the following concentration.

If the catalyst (a), i.e., catalyst comprising the soluble vanadium compound and the organoaluminum compound, is used in the invention, the concentration of the soluble vanadium compound in the polymerization system is in the range of usually 0.01 to 5 mmol/liter-polymerization volume, preferably 0.05 to 3 mmol/liter. The soluble vanadium compound is desirably fed as a solution in a concentration of not more than 10 times, preferably 1 to 7 times, more preferably 1 to 5 times, as much as the concentration of the soluble vanadium compound present in the polymerization system. The organoaluminum compound is fed in a molar ratio of the aluminum atom to the vanadium atom (Al/V) in the polymerization system of not less than 2, preferably 2 to 50, more preferably 3 to 20.

The soluble vanadium compound and the organoaluminum compound [a] are generally fed after diluted with the aforesaid hydrocarbon solvents and/or the α-olefin (ii) in a liquid state and the chain polyene group-containing norbornene compound (iii) in a liquid state.

In this case, the soluble vanadium compound is desirably diluted in the above-mentioned concentration, and the organoaluminum compound is desirably fed after controlling the concentration to an optional concentration of not more than 50 times as much as the concentration of the organoaluminum compound in the polymerization system.

If the catalyst (b), i.e., catalyst comprising the metallocene compound and the organoaluminum oxy-compound or the ionizable ionic compound (also referred to as "ionic ionizable compound" or "ionic compound"), is used, the concentration of the metallocene compound in the polymerization system is in the range of usually 0.00005 to 0.1 mmol/liter-polymerization volume, preferably 0.0001 to 0.05 mmol/liter. The organoaluminum oxy-compound is fed in a molar ratio of the aluminum atom to the transition metal of the metallocene compound (Al/transition metal) in the polymerization system of 1 to 10,000, preferably 10 to 5,000.

In the case of using the ionizable ionic compound, this compound is fed in a molar ratio of the ionizable ionic compound to the metallocene compound (ionizable ionic compound/metallocene compound) in the polymerization system of 0.5 to 20, preferably 1 to 10.

In the case of using the organoaluminum compound, this compound is used in such an amount that the concentration of the organoaluminum compound in the system becomes usually about 0 to 5 mmol/liter-polymerization volume, preferably about 0 to 2 mmol/liter.

When the ethylene (i), the α-olefin (ii) and the chair polyene group-containing norbornene compound (iii) are copolymerized in the presence of the catalyst [a] comprising the soluble vanadium compound and the organoaluminum compound, the copolymerization reaction is carried out under the conditions of a temperature of −50 to 100° C., preferably −30 to 80° C., more preferably −20 to 60° C., and a pressure of more than 0 kg/cm$^2$ and not more than 50 kg/cm$^2$, preferably more than 0 kg/cm$^2$ and not more than 20 kg/cm$^2$.

When the ethylene (i), the α-olefin (ii) and the chain polyene group-containing norbornene compound (iii) are copolymerized in the presence of the catalyst [b] comprising the metallocene compound and the organoaluminum oxy-compound or the ionizable ionic compound, the copolymerization reaction is carried out under the conditions of a temperature of −20 to 150° C., preferably 0 to 120° C., more preferably 0 to 100° C., and a pressure of more than 0 kg/cm$^2$ and not more than 80 kg/cm$^2$, preferably more than 0 kg/cm$^2$ and not more than 50 kg/cm$^2$.

The reaction time (mean residence time in case of continuous copolymerization process) is in the range of usually 5 minutes to 5 hours, preferably 10 minutes to 3 hours, though it varies depending on the conditions such as catalyst concentration and polymerization temperature.

In the present invention, the ethylene (i), the α-olefin (ii) and the chain polyene group-containing norbornene compound (iii) are fed to the polymerization system in such amounts that the unsaturated ethylene copolymer having the aforementioned specific composition is obtained. In the copolymerization, a molecular weight-modifier such as hydrogen can be employed.

When the ethylene (i), the α-olefin (ii) and the chain polyene group-containing norbornene compound (iii) are copolymerized as described above, the unsaturated ethylene copolymer is usually obtained in the form of a polymerization solution containing the copolymer. This polymerization solution is treated in a conventional way to obtain the unsaturated ethylene copolymer.

(Vulcanizable rubber composition)

The rubber composition containing the unsaturated copolymer of ethylene according to the invention is a vulcanizable rubber composition. (The rubber composition of the invention is sometimes referred to as vulcanizable rubber composition hereinafter.) This rubber composition can be used in the unvulcanized state, but if it is used as the vulcanized product, much more improved properties can be exhibited.

The vulcanizable rubber composition according to the invention can be vulcanized by heating it with a vulcanizing agent or irradiating it with electron rays without using a vulcanizing agent.

The vulcanizable rubber composition of the invention may appropriately contain other components according to the purpose in addition to the unsaturated copolymer of ethylene, and it is desired that the unsaturated copolymer of ethylene is contained in an amount of not less than 20% by weight, preferably not less than 25% by weight, based on the whole amount of the rubber composition.

Examples of the other components which may be incorporated into the composition include various chemicals such as reinforcing agents, inorganic fillers, softening agents, antioxidants (stabilizers), processing aids, compounds which constitute a foaming system (e.g., foaming agent and foaming aid), plasticizers, colorants, blowing agents and other rubber additives. The kinds and the amounts of the additives are properly determined depending on the purpose. Of the above additives, preferably used are reinforcing agent, inorganic filler, softening agent, etc. Details of these additives are described below.

Reinforcing Agent and Inorganic Filler

Examples of the reinforcing agents include carbon blacks such as SRF, GPF, FEF, MAF, HAF, ISAF, SAF, FT and MT, surface treated materials obtained by surface treating of the above carbon blacks with silane coupling agents, silica, activated calcium carbonate, powdery talc and powdery silicic acid.

Examples of the inorganic fillers include precipitated calcium carbonate, ground limestone, talc and clay.

The rubber composition of the invention may contain the reinforcing agent and/or the inorganic filler in an amount of usually not more than 300 parts by weight, preferably 10 to 300 parts by weight, more preferably 10 to 200 parts by weight, based on 100 parts by weight of the unsaturated copolymer of ethylene.

From the rubber composition containing the reinforcing agent in the above-mentioned amount, a vulcanized rubber improved in mechanical properties such as tensile strength, tear strength and abrasion resistance can be obtained.

If the inorganic filler is added in the above-mentioned amount, the hardness can be improved without deteriorating other properties of the vulcanized rubber, and the cost can be lowered.

Softening Agent

As the softening agents, those conventionally added to rubbers can be widely used, and examples thereof include:

petroleum type softening agents, such as process oil, lubricant, paraffin, liquid paraffin, petroleum asphalt and vaseline;

coal tar type softening agents, such as coal tar and coal tar pitch;

fatty oil type softening agents, such as castor oil, linseed oil, rapeseed oil and coconut oil;

waxes, such as tall oil, factice, beeswax, carnauba wax and lanolin;

fatty acids and fatty acid salts, such as ricinoleic acid, palmitic acid, barium stearate, calcium stearate and zinc laurate; and synthetic high polymer materials, such as petroleum resin, atactic polypropylene and counarone-indene resin.

Of these, preferred are petroleum type softening agents, and particularly preferred is process oil.

The softening agent may be contained in the rubber composition of the invention in an amount of usually not more than 200 parts by weight, preferably 10 to 200 parts by weight, more preferably 10 to 150 parts by weight, particularly preferably 10 to 100 parts by weight, based on 100 parts by weight of the unsaturated ethylene copolymer.

Antioxidant

The antioxidant is preferably contained in the rubber composition of the invention because the material life can be lengthened.

Examples of the antioxidants include:

aromatic secondary amine type stabilizers, such as phenylnaphthylamine, 4,4-(α,α-dimethylbenzyl) diphenylamine, and N,N'-di-2-naphthyl-p-phenylenediamine;

phenol type stabilizers, such as 2,6-di-t-butyl-4-methylphenol, and tetrakis-(methylene-3-(3',5'-di-t-butyl-4'-hydroxyphenyl)propionate)methane;

thioether type stabilizers, such as bis(2-methyl-4-(3-n-alkylthiopropionyloxy)-5-t-butylphenyl)sulfide;

benzimidazole type stabilizers, such as 2-mercaptobenzimidazole;

dithiocarbamate type stabilizers, such as nickel dibutyldithiocarbamate; and quinoline type stabilizers, such as a polymer from 2,2,4-trimethyl-1,2-dihydroquinoline. These stabilizers may be used in combination of two or more kinds.

The antioxidant may be used in an amount of not more than 5 parts by weight, preferably not more than 3 parts by weight, based on 100 parts by weight of the unsaturated copolymer of ethylene.

Processing Aid

As the processing aids, those conventionally added to rubbers can be widely used. Examples thereof include various acids, such as ricinoleic acid, stearic acid, palmitic acid and lauric acid; salts of these higher fatty acids, such as barium stearate, zinc stearate and calcium stearate; and esters of the above acids.

The processing aid may be used in an amount of not more than 10 parts by weight, preferably not more than 5 parts by weight, based on 100 parts by weight of the unsaturated copolymer of ethylene.

Vulcanizing Agent

When the rubber composition of the invention is vulcanized by heating, compounds which constitute a vulcanization system such as vulcanizing agent, vulcanization accelerator and vulcanization aid are generally added to the rubber composition.

Examples of the vulcanizing agents employable herein include sulfur, sulfur compounds and organic peroxides.

There is no specific limitation on the type of sulfur, and, for example, powdery sulfur, precipitated sulfur, colloidal sulfur, surface-treated sulfur and insoluble sulfur can be employed.

Examples of the sulfur compounds include sulfur chloride, sulfur dichloride, high-molecular weight polysulfide, morpholine disulfide, alkylphenol disulfide, tetramethylthiuram disulfide and selenium dimethyldithiocarbamate.

Examples of the organic peroxides include:

alkyl peroxides, such as dicumyl peroxide, di-t-butyl peroxide, di-t-butylperoxy-3,3,5-trimethylcyclohexane, t-butylcumyl peroxide, di-t-amyl peroxide, 2,5-dimethyl-2,5-di(t-butylperoxine)hexyne-3, 2, S-dimethyl-2,5-di(benzoylperoxy)hexane, 2,5-dimethyl- 2,5-di(t-butylperoxy)hexane, α,α'-bis(t-butylperoxy-m-isopropyl)benzene and t-butyl hydroperoxide;

peroxy esters such as t-butyl peroxyacetate, t-butyl peroxyisobutyrate, t-butyl peroxybivalate, t-butylperoxymaleic acid, t-butyl peroxyneodecanoate, t-butyl peroxybenzoate, and di-t-butyl peroxyphthalate; and ketone peroxides, such as dicyclohexanone peroxide. These organic peroxides may be used in combination of two or more kinds.

Of these, preferred are organic peroxides having a temperature, at which the half-life period thereof is one minute, of 130 to 200° C., for example, dicumyl peroxide, di-t-butyl peroxide, di-t-butylperoxy-3,3,5-trimethylcyclohexane, t-butylcumyl peroxide, di-t-amyl peroxide and t-butyl hydroperoxide.

Of the above-mentioned various vulcanizing agents, sulfur or the sulfur compound, especially sulfur, is preferred in the invention, because particularly improved properties of the rubber composition can be exhibited.

When the vulcanizing agent is sulfur or the sulfur compound, it is used in an amount of 0.1 to 10 parts by weight, preferably 0.5 to 5 parts by weight, based on 100 parts by weight of the unsaturated ethylene copolymer.

When the vulcanizing agent is the organic peroxide, it is used in an amount of 0.0003 to 0.05 mol, preferably 0.001 to 0.03 mol, based on 100 g of the unsaturated ethylene copolymer.

Vulcanization Accelerator

When sulfur or the sulfur compound is used as the vulcanizing agent, a vulcanization accelerator is preferably used in combination.

Examples of the vulcanization accelerators include:

sulfenamide compounds, such as N-cyclohexyl-2-benzothiazole sulfenamide (CBS), N-oxydiethylene-2-benzothiazole sulfenamide and N,N-diisopropyl-2-benzothiazole sulfenamide;

thiazole compounds, such as 2-mercaptobenzothiazole (MBT), 2-(2,4-dinitrophenyl)mercaptobenzothiazole, 2-(2,6-diethyl-4-morpholinothio)benzothiazole and dibenzothiazyl disulfide;

guanidine compounds, such as diphenylguanidine, triphenylguanidine, diorthonitrileguanidine, orthonitrile biguanide and diphenylguanidine phthaliate;

aldehyde amines or aldehyde-ammonia compounds, such as acetaldehyde-aniline reaction product, butylaldehyde-aniline condensate, hexamethylenetetramine and acetaldehyde ammonia;

imidazoline compounds, such as 2-mercaptoimidazoline;

thiourea compounds, such as thiocarbanilide, diethylthiourea, dubutylthiourea, trimethylthiourea and diorthotolylthiourea;

thiuram compounds, such as tetramethylthiuram monosulfide, tetramethylthiuram disulfide (TMTD), tetraethylthiuram disulfide, tetrabutylthiuram disulfide, pentamethylenethiuram tetrasulfide and dipentamethylenethiuram tetrasulfide (DPTT);

dithio acid salt compounds, such as zinc dimethyldithiocarbamate, zinc diethyldithiocarbamate, zinc di-n-butyldithiocarbamate, zinc ethylphenyldithiocabamate, zinc butylphenyldithiocarbamate, sodium dimethyldithiocarbamate, selenium dimethyldithiocarbamate and tellurium dimethyldithiocarbamate;

xanthate compounds, such as zinc dibutylxanthate; and zinc white.

The vulcanization accelerator is desirably used in an amount of 0.1 to 20 parts by weight, preferably 0.2 to 10 parts by weight, based on 100 parts by weight of the unsaturated ethylene copolymer.

Vulcanization Aid (Polyfunctional monomer)

When the organic peroxide is used as the vulcanizing agent, a vulcanization aid is preferably used in an amount of 0.5 to 2 mol based on 1 mol of the organic peroxide, preferably almost in the equimolar amount.

Examples of the vulcanization aids include:

sulfur;

quinonedioxime compounds, such as p-quinonedioxime;

(meth)acrylate compounds, such as trimethylolpropane triacrylate and polyethylene glycol dimethacrylate;

allyl compounds, such as diallyl phthalate and triallyl cyanurate;

maleimide compounds, such as m-phenylene bismaleimide; and divinylbenzene.

Foaming Agent

When the rubber composition of the invention contains a compound which constitutes a foaming system, such as a foaming agent or a foaming aid, the composition can be subjected to foam molding.

As the foaming agents, those conventionally used in the foam molding of rubbers can be widely used. Particular examples thereof include inorganic foaming agents, such as sodium bicarbonate, sodium carbonate, ammonium bicarbonate, ammonium carbonate and ammonium nitrite; nitroso compounds, such as N,N'-dimethyl-N,N'-dinitrosoterephthalamide and N,N'-dinitrosopentamethylenetetramine; azo compounds, such as azodicarbonamide, azobisisobutyronitrile, azocyclohexylnitrile, azodiaminobenzene and barium azodicarboxylate; sulfonylhydrazide compounds, such as benzenesulfonylhydrazide, toluenesulfonylhydrazide, p,p'-oxybis(benzenesulfonylhydrazide) and diphenylsulfone-3,3'-disulfonylhydrazide; azide compounds, such as calcium azide, 4,4-diphenyldisulfonylazide and p-toluenesulfonylazide.

Of these, preferred are nitroso compounds, azo compounds and azide compounds.

The foaming agent may be used in an amount of 0.5 to 30 parts by weight, preferably 1 to 20 parts by weight, based on 100 parts by weight of the unsaturated copolymer of ethylene. From the rubber composition containing the foaming agent in such amount, foamed products having an apparent specific gravity of 0.03 to 0.8 g/cm$^3$ can be produced.

In combination with the foaming agent, a foaming aid can be employed. When the foaming aid is used in combination, various effects such as lowering of decomposition temperature of the foaming agent, acceleration of decomposition thereof and uniformity of the resulting foam can be exerted. Examples of the foaming agents include organic acids, such as salicylic acid, phthalic acid, stearic acid and oxalic acid, urea and its derivative.

The foaming aid may be used in an amount of 0.01 to 10 parts by weight, preferably 0.1 to 5 parts by weight, based on 100 parts by weight of the unsaturated copolymer of ethylene.

Other Rubber

The rubber composition of the invention may contain other known rubbers as long as the objects of the invention are not marred.

Examples of such rubbers include natural rubbers (NR); isoprene type rubbers, such as isoprene rubber (IR); and conjugated diene type rubbers, such as butadiene rubber (BR), styrene-butadiene rubber (SBR), acrylonitrile-butadiene rubber (NBR) and chloroprene rubber (CR).

Also employable are conventionally known ethylene-α-olefin copolymer rubbers, for example, ethylene-propylene random copolymer (EPR) and ethylene-α-olefin-polyene terpolymer other than the unsaturated copolymer of ethylene, such as EPDM.

The vulcanizable rubber composition of the invention can be prepared from the unsaturated copolymer of ethylene and the above-mentioned other components by conventional processes for preparing rubber blends. For example, the unsaturated copolymer of ethylene and other components are kneaded at 80 to 170° C. for 3 to 10 minutes using an internal mixer such as Banbury mixer, kneader and intermixer, then the vulcanizing agent and the vulcanization accelerator or the vulcanization aid are added if necessary, and the resulting mixture is kneaded at a roll temperature of 40 to 80° C. for 5 to 30 minutes using a roll (e.g., an open roll) or a kneader, followed by delivering. Thus, a rubber composition (rubber blend) in the form of usually ribbon or sheet can be obtained. If the temperature for kneading by the use of the internal mixer is low, the vulcanizing agent, the vulcanization accelerator and the foaming agent may be simultaneously kneaded.

(Vulcanized rubber)

A vulcanizate (vulcanized rubber) of the rubber composition of the invention can be obtained by generally preforming the unvulcanized rubber composition into a desired shape using various means such as an extrusion molding machine, a calender roll, a press, an injection molding machine and a transfer molding machine, and simultaneously or thereafter heating the preform in a vulcanizing bath or irradiating it with electron rays so as to vulcanize it.

When the rubber composition is vulcanized by heating, the rubber composition is preferably heated at a temperature of 150 to 270° C. for 1 to 30 minutes using a heating bath of hot air, glass bead fluidized bed, UHF (ultrahigh frequency electromagnetic wave), steam or LCM (molten salt bath).

When the rubber composition is vulcanized by irradiation with electron rays without using a vulcanizing agent, the preformed rubber composition is irradiated with electron rays having energy of 0.1 to 10 MeV, preferably 0.3 to 2 MeV at an absorbed dose of 0.5 to 35 Mrad, preferably 0.5 to 10 Mrad.

In the preforming and vulcanization, a mold may be used or may not be used.

If a mold is not used, forming and vulcanization of the rubber composition are generally carried out continuously.

The rubber composition thus formed and vulcanized can be used for automotive industrial parts such as weatherstrip, door glass run channel, window frame, radiator hose, brake parts and wiper blade; industrial rubber parts such as rubber roll, belt, packing and hose; electrical insulating materials such as anode cap and grommet; civil engineering and building materials such as building gasket and civil engineering sheet; and rubberized fabrics.

The vulcanized foamed product obtained by foaming the rubber blend containing the foaming agent under heating can be used for heat insulating materials, cushioning materials, sealing materials, etc.

EFFECT OF THE INVENTION

According to the invention, a chain polyene group-containing norbornene compound suitably used for preparing a novel unsaturated ethylene copolymer being excellent in weathering resistance, heat resistance and ozone resistance and having a high vulcanizing rate can be obtained. According to the invention, further, an unsaturated ethylene copolymer having good balance of the above-mentioned properties can be obtained.

EXAMPLE

The present invention will be further described with reference to the following examples, but it should be construed that the invention is in no way limited to those examples.

(1) In the following examples to prepare polymers, a substance (EMHN-containing substance), which contains, for example, not only EMHN (5-(2-ethylidene-6-methyl-5-heptenyl)-2-norbornene) (true EMHN) obtained by the following examples to synthesize monomers but also a small amount of a by-product (5-[3,7-dimethyl-2,6-octadienyl]-2-norbornene), is used as EMHN. Therefore, the term "EMHN"sometimes means a mixture (EMHN-containing substance) of the true EMHN and the by-product, and the term "ethylene/propylene/EMHN copolymer" sometimes means a copolymer containing true EMHN units and units derived from the by-product (EMHN-containing units) as the EMHN units, unless use of these terms does not depart from the objects of the invention.

(2) The proportions of the constituent units [II] derived from EMHN (I) as the main component and the constituent units [II-a] derived from the by-product [I-a] were determined in the following way.

Measuring Device and Measuring Conditions

Device

NMR: GSH-270 model, FT-NMR, manufactured by Japan Electron Optics Laboratory Co., Ltd.

Main conditions of $^1$H-NMR spectrum measurement

Observation range: 5,400 Hz (20 ppm)

Pulse width: 7.3 μsec (45°)

Solvent: hexachlorobutadiene

Rock solvent: deuterated benzene

Measuring mode: proton non-decoupling

Measuring temperature: 120° C.

Concentration: 50 mg/0.4 cc

Number of integrating times: 1,000 to 3,000

Calculation

The area of 5.07 to 5.17 ppm region is taken as S1.
The area of 5.17 to 5.35 ppm region is taken as S2.

The proportion (% by mol) of the constituent units [II] derived from the compound [I] as the main component and the proportion (% by mol) of the constituent units [II-a] derived from the by-product [I-a] are calculated by the following equations.

[I]: [S2×2/(S1+S2)]×100

[II-a]: [(S1−S2)/(S1+S2)]×100

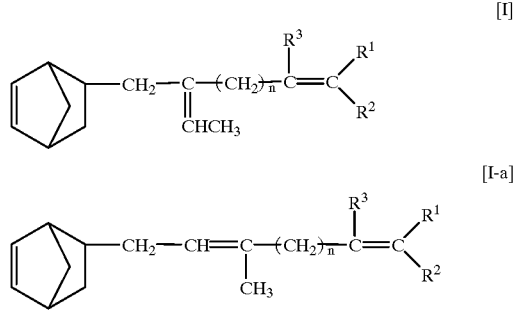

Reference Example 1

Preparation of Catalyst

A 50-ml flask equipped with a stirrer was charged with 43 mg (0.33 mmol) of anhydrous cobalt(II) chloride, 263 rg (0.66 mmol) of 1,2-bis(diphenylphosphino)ethane and 23 ml of anhydrous decane in an argon atmosphere, and they were stirred at 25° C. for 2 hours. Then, 17 ml of a triethylaluminum/toluene solution (concentration: 1 mol/liter, triethylaluminum: 17 mmol) was added, and the mixture was stirred at the above temperature (25° C.) for 2 hours to prepare a catalyst.

Synthesis of 4-ethylidene-8-methyl-1,7-nonadiene (EMN)

EMN represented by the following formula was synthesized in the manner described below.

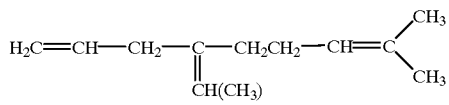

Into a 300-ml stainless steel (SUS316) autoclave 100 g (734 mmol) of 7-methyl-3-methylene-1,6-octadiene (β-myrcene) and the total amount of the above-prepared catalyst were introduced in an argon atmosphere, and the autoclave was sealed.

Then, an ethylene bomb was connected (directly) to the autoclave, and ethylene was fed to the autoclave until the internal pressure of the autoclave became 35 kg/cm$^2$.

Then, the autoclave was heated to 95° C. to perform reaction. During the reaction, ethylene was intermittently added to the autoclave five times to make up for the consumed ethylene to thereby run the reaction for 15 hours in total.

After the reaction was completed, the autoclave was cooled and then released. The resulting reaction mixture was poured into 100 ml of water to separate it into an organic phase and an aqueous phase.

The organic phase thus separated was withdrawn, distilled by an evaporator to remove low-boiling substances and then subjected to 20-plate precision vacuum distillation, to obtain 83 g of the desired EMN (yield: 69%, β-myrcene conversion ratio: 90%).

Additionally, 16 g of 5,9-dimethyl-1,4,8-decatriene (yield: 13%) was produced as a by-product.

The results of analysis of the 4-ethylidene-8-methyl-1,7-nonadiene (EMN) obtained above are as follows.

(1) Boiling point: 103 to 105° C./30 mmHg (2) GC-MS (gas chromatography mass spectrometry):
m/z 164 (M$^+$ molecule ion peak),
149, 123, 95, 69, 41, 27

Measuring Conditions of Gas Chromatography

Column: capillary column DB-1701 (0.25 mm×30 m), available from J & W Scientific Co.

Vaporization temperature: 250° C.

Column temperature: maintained at 60° C. for 5 min, then raised up to 200° C. at 10° C./min (3) Infrared absorption spectrum (neat, cm$^{-1}$) absorption peaks: 3080, 2975, 2925, 2850, 1670, 1640, 1440, 1380, 1235, 1110, 995, 910, 830

(4) $^1$H-NMR spectrum (solvent: CDCl$_3$)
The absorption peaks are described below.

TABLE 1

| ppm (δ) | Proton number, Peak |
| --- | --- |
| 1.59 | (3H, doublet, J = 7 Hz) |
| 1.60 | (3H, singlet) |
| 1.68 | (3H, singlet) |
| 2.00 | (2H, multiplet) |
| 2.06 | (2H, multiplet) |
| 2.80 | (2H, doublet, J = 7 Hz) |

TABLE 1-continued

| ppm (δ) | Proton number, Peak |
|---|---|
| 4.9–5.2 | (3H, multiplet) |
| 5.30 | (1H, quartet, J = 7 Hz) |
| 5.75 | (1H, multiplet) |

Example 1

Synthesis of 5-(2-ethylidene-6-methyl-5-heptenyl)-2-norbornene (EMHN, chain polyene group-containing norbornere compound (11) exemplified above)

Into a 1-liter stainless steel autoclave, 240.7 g (1.156 mol) of 4-ethylidene-8-methyl-1,7-nonadiene (EMN) obtained in Reference Example 1 was introduced. Then, to the autoclave was introduced 153.0 g (2.314 mol) of cyclopentadiene over a period of 5 hours, with stirring EMN under heating at 190° C. and a nitrogen pressure of 2 kg/cm².

The system was then heated at 190° C. for 1 hour with stirring and cooled to room temperature, followed by releasing the autoclave.

The reaction mixture thus obtained was subjected to vacuum distillation to remove low-boiling substances, and the residue was subjected to 40-plate precision vacuum distillation to obtain 53.8 g of the desired EMHN (5-(2-ethylidene-6-methyl-5-heptenyl)-2-norbornene). The yield was 20.2% on the basis of 4-ethylidene-8-methyl-1,7-nonadiene.

Additionally, 10.1 g of [5-(3,7-dimethyl-2,6-octadienyl)]-2-norbornene was obtained as a by-product. Therefore, the ratio of EMHN to the by-product was 5.33/1.

The physiochemical data of the EMHN are as follows.

(1) Boiling point: 138° C./3 mmHg
(2) Gas chromatography mass spectrometry:
m/z 230 (M⁺), 215, 187, 123, 91, 69

Measuring Conditions of Gas Chromatography

Column: capillary column DB-1701 (0.25 mm×30 m), available from J & W Scientific Co.

Vaporization temperature: 250° C.

Column temperature: maintained at 40° C. for 5 min, then raised up to 200° C. at 5° C./min (3) Infrared absorption spectrum (neat, cm⁻¹)
3050, 2960, 2925, 2850, 1660, 1630, 1570, 1440, 1375, 1345, 1330, 1250, 1220, 1100, 980, 925, 900, 820, 780, 715

(4) Proton NMR spectrum (CDCl₃ solvent)
The absorption peaks are described below.

TABLE 2

| ppm (δ) | Proton number, Peak |
|---|---|
| 0.55 | (1H, multiplet) |
| 1.1–2.3 | (10H, multiplet) |
| 1.55 | (3H, doublet, J = 7 Hz) |
| 1.60 | (3H, singlet) |
| 1.67 | (3H, singlet) |
| 2.7 | (2H, multiplet) |
| 5.10 | (1H, multiplet) |

TABLE 2-continued

| ppm (δ) | Proton number, Peak |
|---|---|
| 5.20 | (1H, quartet, J = 7 Hz) |
| 5.9–6.2 | (2H, multiplet) |

Example 2

Into a 1-liter stainless steel autoclave, 153.0 g (1.157 mol) of dicyclopentadiene and 240.7 g (1.156 mol) of 4-ethylidene-8-methyl-1,7-nonadiene were introduced, and they were stirred under heating at 190° C. for 6 hours under a nitrogen pressure of 2 kg/cm² to perform reaction.

After the reaction was completed, the system was cooled to room temperature and the autoclave was released. The reaction mixture thus obtained was subjected to vacuum distillation to remove low-boiling substances, and the residue was subjected to 40-plate precision vacuum distillation to obtain 48.7 g of the desired EMHN. The yield was 18.3% on the basis of 4-ethylidene-8-methyl-1,7-nonadiene.

Additionally, 9.7 g of 5-[3,7-dimethyl-2,6-octadienyl]-2-norbornene was obtained as a by-product. Therefore, the ratio of EMHN to the by-product was 5.02/1.
Reference

[5-(3,7-dimethyl-2,6-octadienyl]-2-norbornene
(1) Proton NMR spectrum (CDCl₃ solvent):
0.55 (1H, multiplet)
1.0–2.3 (8H, multiplet)
1.60 (6H, singlet)
1.68 (3H, singlet)
2.7 (2H, multiplet)
5.1 (2H, multiplet)
5.9–6.2 (2H, multiplet)
(2) Infrared absorption spectrum (neat, cm⁻¹)
3050, 2960, 2925, 2860, 1670, 1640, 1450, 1380, 1340, 1250, 1105, 900, 830, 720

Example 3

In a 2-liter polymerizer equipped with a stirring blade, terpolymerization reaction of ethylene, propylene and EMHN (5-(2-ethylidene-6-methyl-5-heptenyl)-2-norbornene) obtained in Example 1 was continuously carried out.

This polymerization reaction was carried out in the following manner.

To the polymerizer were continuously fed, from the top thereof, a hexane solution of the EMHN-containing substance at a feed rate of 0.5 l/hr so that the concentration in the polymerizer became 15 mmol/l, a hexane solution of VO(OC₂H₅)Cl₂ as a catalyst at a feed rate of 0.5 l/hr so that the vanadium concentration in the polymerizer became 0.2 mmol/l, a hexane solution of ethylaluminum sesquichloride (Al(C₂H₅)₁.₅Cl₁.₅) as a catalyst at a feed rate of 0.5 l/hr so that the aluminum concentration in the polymerizer became 2.0 mmol/l, and hexane at a feed rate of 0.5 l/hr. On the other hand, the polymer solution was continuously drawn out from the top of the polymerizer so that the polymer solution in the polymerizer was kept constant in an amount of 1 liter.

To the polymerization system were further fed ethylene at a feed rate of 140 l/hr, propylene at a feed rate of 160 l/hr and hydrogen at a feed rate of 15 l/hr using bubbling tubes. The copolymerization reaction was conducted at 30° C. by circulating a cooling medium through a jacket provided outside the polymerizer.

Through the copolymerization reaction under the above conditions, a polymer solution containing an ethylene/propylene/EMHN-containing substance copolymer was obtained.

The polymer solution thus obtained was deashed using hydrochloric acid and then introduced into a large amount of methanol to precipitate the polymer, followed by vacuum drying at 100° C. for 24 hours.

Thus, an ethylene/propylene/EMHN-containing substance copolymer was obtained in an amount of 68 g per hour.

In the copolymer, the ethylene constituent units were contained in an amount of 67.2% by mol, the propylene constituent units were contained in an amount of 31.6% by mol, the constituent units derived from the EMHN-containing substance were contained in an amount of 1.2% by mol, and the molar ratio of the ethylene constituent unit/propylene constituent unit was 68/32. The intrinsic viscosity [η] of the copolymer was 2.5 dl/g.

The amount (1.2% by mol) of the EMHN-containing substance constituent units were composed of 0.85% by mol of EMHN constituent units and 0.35% by mol of constituent units derived from a by-product ([5-(3,7-dimethyl-2,6-octadienyl)]-2-norbornene).

Then, a composition containing 100 parts by weight of the ethylene/propylene/EMHN-containing substance copolymer, 5 parts by weight of zinc white No. 1, 1 part by weight of stearic acid, 80 parts by weight of N330 (trade name: Seast 3, available from Tokai Carbon K.K.), 50 parts by weight of oil (trade name: Santhen 4240, available from San Oil K.K.), 1.0 part by weight of a vulcanization accelerator A (trade name: Nocceller TT, available from Ouchi Shinko Kagaku K.K.), 0.5 part by weight of a vulcanization accelerator B (trade name: Nocceller M, available from Ouchi Shinko Kagaku K.K.) and 1.5 parts by weight of sulfur as shown in the following table was kneaded by a 6-inch open roll to obtain an unvulcanized rubber blend (unvulcanized rubber composition).

The ingredients of the unvulcanized rubber blend are set forth in Table 3.

Estimation of a vulcanizing rate (T90 (min)) of the rubber blend resulted in 6.1.

The result is set forth in Table 4.

The vulcanizing rate was determined in the following manner. As a measuring device, JSR curelastometer 3 model (Japan Synthetic Rubber Co., Ltd.) was used. A difference between the maximum value MH and the minimum value ML of the torque obtained from the vulcanization curve was taker as ME (ME=MH−ML), and the vulcanizing rate was estimated in terms of the period of time (T90 (min)) required for the difference ME to reach 90% ME. Estimation of T90 (min) of the above rubber blend resulted in 6.1.

Subsequently, the unvulcanized rubber blend obtained by blending the ingredients shown in Table 3 was press vulcanized at 160° C. for a period of T90 (min)+2 min (i.e., 6.8+2=8.8 (min)), and the properties of the resulting vulcanized rubber were measured. That is, T90 (min) of the unvulcanized rubber blend and the properties of the vulcanized rubber were evaluated.

The vulcanized rubber had a 100% modulus (M100, kgf/cm$^2$) of 35, a 200% modulus (M200, kgf/cm$^2$) of 85, a 300% modulus (M300, kgf/cm$^2$) of 125, a tensile strength (T$_B$, kgf/cm$^2$) of 195, an elongation (E$_B$, %) of 460 and a hardness (H$_S$, JIS A) of 68.

The results are set forth in Table 4.

The above properties were all measured in accordance with JIS K 6301.

TABLE 3

| Ingredients of Unvulcanized Rubber Blend | Part(s) by weight |
|---|---|
| Ethylene/propylene/EMHN copolymer | 100 |
| Zinc white No. 1 | 5 |
| Stearic acid | 1 |
| N330 | 80 |
| (Seast 3, from Tokai Carbon K.K.) | |
| Oil (Santhen 4240, from San Oil K.K.) | 50 |
| Vulcanization accelerator A | 1.0 |
| (Nocceller TT, from Ouchi Shinko Kagaku K.K.) | |
| Vulcanization accelerator B | 0.5 |
| (Nocceller M, from Ouchi Shinko Kagaku K.K.) | |
| Sulfur | 1.5 |

Example 4

Copolymerization reaction was carried out in the same manner as in Example 3 except that the EMHN-containing substance was fed so that the concentration in the polymerizer became 5.9 mmol/l, ethylene was fed at a feed rate of 130 l/hr, and propylene was fed at a feed rate of 170 l/hr, to thereby obtain an ethylene/propylene/EMHN-containing substance copolymer in an amount of 79 g per hour.

In the copolymer thus obtained, the ethylene constituent units were contained in an amount of 62.2% by mol, the propylene constituent units were contained in an amount of 37.3% by mol, the constituent units derived from the EMHN-containing substance were contained in an amount of 0.55% by mol, and the molar ratio of the ethylene constituent unit/propylene constituent unit was 63/37. The intrinsic viscosity [η] of the copolymer was 2.1 dl/g.

The amount (0.55% by mol) of the EMHN-containing substance constituent units were composed of 0.38% by mol of EMHN constituent units and 0.17% by mol of constituent units derived from a by-product ([5-(3,7-dimethyl-2,6-octadienyl)]-2-norbornene).

Then, an unvulcanized rubber blend was obtained in the same manner as in Example 3 except that the above-obtained copolymer was used in place of the ethylene/propylene/EMHN-containing substance copolymer of Example 3.

Estimation of a vulcanizing rate (T90 (min)) of the rubber blend resulted in 7.7.

The unvulcanized rubber blend was obtained in the same manner as in Example 3 except that the above-obtained ethylene/propylene/EMHN-containing substance copolymer was used. The unvulcanized rubber blend was then press molded.

The properties of the resulting vulcanized rubber are described below.

M100: 27, M200: 70, M300: 101, tensile strength (T$_B$): 161, elongation (E$_B$): 530, hardness (H$_S$): 67

The results are set forth in Table 4.

Comparative Example 1

In a 2-liter polymerizer equipped with a stirring blade, copolymerization reaction of ethylene, propylene and 5-ethylidene-2-norbornene (ENB) was continuously carried out.

In detail, to the polymerizer were continuously fed, from the top thereof, a hexane solution of ENB (7.1 g/l) at a feed rate of 0.5 l/hr, a hexane solution of VO(OC$_2$H$_5$)Cl$_2$ (0.8 mmol/l) as a catalyst at a feed rate of 0.5 l/hr, a hexane solution of ethylaluminum sesquichloride (Al($C_2H_5$)$_{1.5}Cl_{1.5}$) (8.0 mmol/l) as a catalyst at a feed rate of 0.5 l/hr and hexane at a feed rate of 0.5 l/hr. On the other hand, the polymer solution was continuously drawn out from the top of the polymerizer so that the polymer solution in the polymerizer was kept constant in an amount of 1 liter. To the polymerization system were further fed ethylene at a feed rate of 120 l/hr, propylene at a feed rate of 180 l/hr and hydrogen at a feed rate of 5 l/hr using bubbling tubes. The copolymerization reaction was conducted at 30° C. by circulating a cooling medium through a jacket provided outside the polymerizer. Through the copolymerization reaction under the above conditions, a polymer solution containing an ethylene/propylene/ENB copolymer was obtained.

The polymer solution thus obtained was deashed using hydrochloric acid and then introduced into a large amount of methanol to precipitate the polymer, followed by vacuum drying at 100° C. for 24 hours.

Thus, an ethylene/propylene/ENB copolymer was obtained in an amount of 64.8 g per hour.

In the copolymer thus obtained, the ethylene constituent units were contained in an amount of 66.8% by mol, the propylene constituent units were contained in an amount of 31.4% by mol, the ENB constituent units were contained in an amount of 1.8% by mol, and the molar ratio of the ethylene constituent unit/propylene constituent unit was 68/32. The intrinsic viscosity [η] of the copolymer was 2.2 dl/g.

Estimation of a vulcanizing rate (T90 (min)) of the rubber blend resulted in 11.2.

Further, an unvulcanized rubber blend was prepared in the same manner as in Example 3 except that the above-obtained copolymer was used, and then press molded.

The properties of the resulting vulcanized rubber are described below.

M100: 30, M200: 74, M300: 117, tensile strength ($T_B$): 168, elongation ($E_B$): 400, hardness ($H_S$): 68

The results are set forth in Table 4.

Example 5

Into a 2-liter stainless steel autoclave thoroughly purged with nitrogen, 900 ml of heptane and 15 ml of the EMHN-containing substance obtained in Example 1 were introduced. Then, propylene was further introduced so that the internal pressure of the system became 3.5 kg/cm$^2$-G at 80° C.

To the system was then fed ethylene until the pressure of the system became 8 kg/cm$^2$-G.

Subsequently, 1 mmol of triisobutylaluminum, 0.005 mmol of triphenylcarbeniumtetrakis(pentafluorophenyl) borate and 0.001 mmol of [dimethyl(t-butylamide) (tetramethylcyclo-pentadienyl)silane]titanium dichloride were pressed into the system with nitrogen to initiate the polymerization.

Then, only ethylene was continuously fed so that the total pressure was kept at 8 kg/cm$^2$-G, and the polymerization was continued at 80° C. for 20 minutes. A small amount of ethanol was added to the system so as to terminate the polymerizatin reaction, and the unreacted monomers were purged out.

The resulting polymer solution was introduced into a large excess of methanol to precipitate a polymer.

The polymer thus precipitated was recovered by filtration and mixed with 30 mg of Irganox 1010 (stabilizer, available from Ciba-Geigy Corporation) and 60 mg of Mark 329k (stabilizer, available from Asahi Denka K.K.). Then, the mixture was dried at 120° C. for one night under reduced pressure.

As a result, 60.1 g of an ethylene/propylene/EMHN-containing substance copolymer was obtained. This copolymer contained 64.9% by mol of ethylene units, 33.7% by mol of propylene units and 1.4% by mol of EMHN-containing substance units, and had a molar ratio of the ethylene units to the propylene units of 65.8/34.2 (ethylene units/propylene units) and an intrinsic viscosity [η] of 3.01 dl/g.

The amount (1.4% by mol) of the EMHN-containing substance constituent units were composed of 1.0% by mol of EMHN constituent units and 0.4% by mol of constituent units derived from a by-product ([5-(3,7-dimethyl-2,6-octadienyl)]-2-norbornene).

Estimation of a vulcanizing rate (T90 (min)) of the rubber blend resulted in 5.4.

Further, an unvulcanized rubber blend was prepared in the same manner as in Example 3 except that the above-obtained copolymer was used, and then press molded.

The properties of the resulting vulcanized rubber are described below.

M100: 45, M200: 93, M300: 135, tensile strength ($T_B$): 170, elongation ($E_B$): 420, hardness ($H_S$): 69.

The results are set forth in Table 4.

Example 6

Polymerization was carried out in the same manner as in Example 5 except that the amount of heptane was varied to 900 ml, 100 ml of 1-octene was introduced in place of propylene, and the polymerization time was varied to 15 minutes. As a result, 48 g of an ethylene/1-octene/EMHN-containing substance copolymer was obtained. This copolymer contained 78.6% by mol of ethylene units, 19.7% by mol of 1-octene units and 1.7% by mol of EMHN-containing substance units, and had a molar ratio of the ethylene units to the 1-octene units of 80.0/20.0 (ethylene units/1-octene units) and an intrinsic viscosity [η] of 2.21 dl/g.

The amount (1.7% by mol) of the EMHN-containing substance constituent units were composed of 1.2% by mol of EMHN constituent units and 0.5% by mol of constituent units derived from a by-product ([5-(3,7-dimethyl-2,6-octadienyl)]-2-norbornene).

Estimation of a vulcanizing rate (T90 (min)) of the rubber blend resulted in 5.9.

Further, an unvulcanized rubber blend was prepared in the same manner as in Example 3 except that the above-obtained copolymer was used, and then press molded.

The properties of the resulting vulcanized rubber are described below.

M100: 38, M200: 90, M300: 132, tensile strength ($T_B$): 150, elongation ($E_B$): 380, hardness ($H_S$): 67.

The results are set forth in Table 4.

Example 7

Polymerization was carried out in the same manner as in Example 5 except that 1-butene was introduced in place of propylene so that the internal pressure of the system became 3.7 kg/cm$^2$-G at 80° C., and the polymerization time was varied to 30 minutes.

As a result, 54 g of an ethylene/1-butene/EMHN-containing substance copolymer was obtained. This copolymer contained 68.0% by mol of ethylene units, 30.6% by mol of 1-butene units and 1.4% by mol of EMHN-containing substance units, and had a molar ratio of the ethylene units to the 1-butene units of 69.0/31.0 (ethylene units/1-butene units) and an intrinsic viscosity [η] of 2.51 dl/g.

The amount (1.4% by mol) of the EMHN-containing substance constituent units were composed of 0.98% by mol of EMHN constituent units and 0.42% by mol of constituent units derived from a by-product ([5-(3,7-dimethyl-2,6-octadienyl)]-2-norbornene).

Estimation of a vulcanizing rate (T90 (min)) of the rubber blend resulted in 6.0.

Further, an unvulcanized rubber blend was prepared in the same manner as in Example 3 except that the above-obtained copolymer was used, and then press molded.

The properties of the resulting vulcanized rubber are described below.

M100: 33, M200: 82, M300: 120, tensile strength ($T_B$): 185, elongation ($E_B$): 470, hardness ($H_S$): 66.

The results are set forth in Table 4.

Example 8

Synthesis of [5-(2-ethylidene-6-methyl-5-heptenyl)]-2-norbornene (EMHN)

Into a 1-liter stainless steel autoclave, 316 g (1.83 mol) of the 4-ethylidene-8-methyl-1,7-nonadiene (EMN, purity: 95%) obtained in Example 2 and 24.2 g (0.183 mol) of dicyclopentadiene (DCPD) were introduced, and they were reacted at 220° C. for 2 hours under a nitrogen pressure of 2 kg/cm². Then, the system was cooled to room temperature, and the autoclave was released. The analysis of the reaction product by means of gas chromatography under the same measuring conditions as described in the Reference Example resulted in a DCPD conversion ratio of 96% and a selectivity of the desired EMHN (on the basis of cyclopentadiene) of 57%. The reaction mixture was subjected to simple distillation under reduced pressure to remove EMN remaining in the reaction mixture, and the residue was subjected to 40-plate precision vacuum distillation. Thus, an EMHN-containing substance was obtained in an amount of 43 g, and the desired EMHN was obtained in an amount of 40.9 g (isolated yield: 48%, on the basis of cyclopentadiene).

Additionally, 2.1 g of [5-(3,7-dimethyl-2,6-octadienyl)]-2-norbornene was obtained as a by-product. Therefore, the ratio of EMHN to the by-product was 19.5/1 (EMHN/by-product).

The physiochemical data of the EMHN are as follows.

Boiling point: 138° C./3 mmHg

Gas chromatography mass spectrometry:

m/z 230 (M⁺), 215, 187, 123, 91, 69

Measuring conditions of gas chromatography: the same as in Reference Example 1

Infrared absorption spectrum (neat, cm⁻¹) 3050, 2960, 2925, 2850, 1660, 1630, 1570, 1440, 1375, 1345, 1330, 1250, 1220, 1100, 980, 925, 900, 820, 780, 715

Proton NMR spectrum (CDCl₃ solvent, 500 MHz NMR)

0.55 (1H, multiplet)

1.1–2.3 (10H, multiplet)

1.55 (3H, doublet, J=7 Hz)

1.60 (3H, singlet)

1.67 (3H, singlet)

2.7 (2H, multiplet)

5.10 (1H, multiplet)

5.20 (1H, quartet, J=7 Hz)

5.9–6.2 (2H, multiplet)

Example 9

Copolymerization was carried out in the same marner as in Example 3 except that an EMHN-containing substance having a purity of 95% was used, to thereby obtain an ethylene/propylene/EMHN-containing substance copolymer in an amount of 65 g per hour.

In the copolymer thus obtained, the ethylene constituent units were contained in an amount of 67.9% by mol, the propylene constituent units were contained in an amount of 30.9% by mol, the EMHN-containing substance constituent units were contained in an amount of 1.2% by mol, and the molar ratio of the ethylene constituent unit/propylene constituent unit was 69/31. The intrinsic viscosity [η] of the copolymer was 2.6 dl/g.

The amount (1.2% by mol) of the EMHN-containing substance constituent units were composed of 1.0% by mol of EMHN constituent units and 0.2% by mol of constituent units derived from a by-product ([5-(3,7-dimethyl-2,6-octadienyl)]-2-norbornene).

Then, the ethylene/propylene/EMHN-containing substance copolymer was blended with other ingredients in the sane manner as in Example 3 to obtain a rubber blend. Estimation of a vulcanizing rate T90 (min) of the rubber blend resulted in 6.2.

The unvulcanized rubber blend was prepared in the same manner as in Example 3 except that the above-obtained copolymer was used, and then press molded.

The properties of the resulting vulcanized rubber are described below.

M100: 36, M200: 87, M300: 128, tensile strength ($T_B$): 196, elongation ($E_B$): 470, hardness ($H_S$): 68.

The results are set forth in Table 4.

TABLE 4

| Properties of vulcanized rubber | Ex. 3 | Ex. 4 | Ex. 5 | Ex. 6 | Ex. 7 | Ex. 9 | Comp Ex. 1 |
|---|---|---|---|---|---|---|---|
| $M_{100}$ | 35 | 27 | 45 | 38 | 33 | 36 | 30 |
| $M_{200}$ | 85 | 70 | 93 | 90 | 82 | 87 | 74 |
| $M_{300}$ | 125 | 101 | 135 | 132 | 120 | 128 | 117 |
| $T_B$ | 195 | 161 | 170 | 150 | 185 | 196 | 168 |
| $E_B$ | 460 | 530 | 420 | 380 | 470 | 470 | 400 |
| $H_S$ | 68 | 67 | 69 | 67 | 66 | 68 | 68 |
| $T_{90}$ (minute) | 6.1 | 7.7 | 5.4 | 5.9 | 6.0 | 6.2 | 11.2 |

Remarks in Table 4
$M_{100}$: 100% tensile modulus (kgf/cm²)
$M_{200}$: 200% tensile modulus (kgf/cm²)
$M_{300}$: 300% tensile modulus (kgf/cm²)
$T_B$: tensile strength (kgf/cm²)
$E_B$: elongation (%)
$H_S$: hardness (measured in accordance with JIS A)
$T_{90}$ (min): vulcanizing rate (min) measured at 160° C.

What is claimed is:

1. A chain polyene group-containing norbornene compound represented by the formula (I):

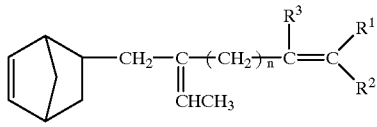

wherein n is an integer of 1 to 5, $R^1$ is a hydrogen atom or an alkyl group of 1 to 5 carbon atoms, and $R^2$ and $R^3$ are each independently a hydrogen atom or an alkyl group of 1 to 5 carbon atoms, provided that $R^1$ and $R^2$ are not hydrogen at the same time.

2. A process for preparing a chain polyene group-containing norbornene compound as claimed in claim 1, comprising reacting cyclopentadiene with a branched chain polyene compound represented by the formula:

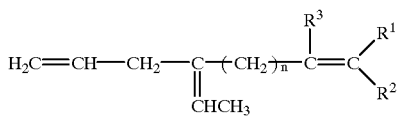

wherein n is an integer of 1 to 5, $R^1$ is an alkyl group of 1 to 5 carbon atoms, and $R^2$ and $R^3$ are each independently a hydrogen atom or an alkyl group of 1 to 5 carbon atoms.

3. An unsaturated ethylene copolymer wherein:

(A) said copolymer is a random copolymer of
  (i) ethylene,
  (ii) an α-olefin of 3 to 20 carbon atoms, and
  (iii) at least one chain polyene group-containing norbornene compound represented by formula (I) of claim 1;

(B) said copolymer comprises:
  (i) constituent units derived from said ethylene in an amount of 30 to 92% by mol,
  (ii) constituent units derived from said α-olefin of 3 to 20 carbon atoms in an mount of 6 to 70% by mol, and
  (iii) constituent units derived from said chain polyene group-containing norbornene compound represented by formula (I) of claim 1 in an amount of 0.1 to 30% by mol, in which
  (iv) the molar ratio of (i) said constituent units derived from said ethylene/(ii) said constituent units derived from said α-olefin of 3 to 20 carbon atoms is in the range of 40/60 to 92/8;

(C) said constituent unit derived from the chain polyene-group containing norbornene compound represented by formula (I) of claim 1 has a structure represented by the following formula:

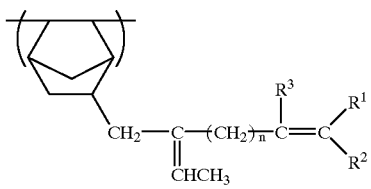

wherein n is an integer of 1 to 5, $R^1$ is an alkyl group of 1 to 5 carbon atoms, and $R^2$ and $R^3$ are each independently a hydrogen atom or an alkyl group of 1 to 5 carbon atoms; and (D) said copolymer has an intrinsic viscosity (η), as measured in Decalin at 135° C., of 0.05 to 10 dl/g.

4. A process for preparing an unsaturated ethylene copolymer as claimed in claim 3, comprising copolymerizing:
  (i) ethylene,
  (ii) an α-olefin of 3 to 20 carbon atoms, and
  (iii) at least one chain polyene group-containing norbornene compound represented by formula (I) of claim 1, in the presence of a catalyst formed from a transition metal compound, an organoaluminum compound and/or an ionizable ionic compound.

5. An unsaturated ethylene copolymer wherein:

(A) said copolymer is a random copolymer of
  (i) ethylene,
  (ii) an α-olefin of 3 to 20 carbon atoms, and
  (iii) at least one chain polyene group-containing norbornene compound represented by formula (I) of claim 1 and at least one chain polyene group-containing norbornene compound represented by the following formula (I-a) in a smaller amount than that of the chain polyene group-containing norbornene compound (I),

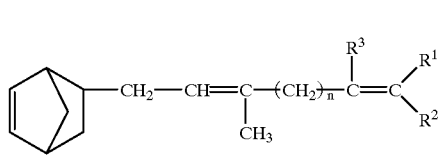

wherein n, $R^1$, $R^2$ and $R^3$ have the same meaning as in the formula (I);

(B) The said copolymer comprises:
  (i) constituent units derived from said ethylene in an amount of 30 to 92% by mol,
  (ii) constituent units derived from said α-olefin 3 to 20 carbon atoms in an amount of 6 to 70% by mol, and
  (iii) constituent units derived from said chain polyene group-containing norbornene compound represented by formula (I) of claim 1 and constituent units derived from said chain polyene group-containing norbornene compound represented by the formula (I-a) in a smaller amount than that of the chain polyene group-containing norbornene compound (I) in the total amount of 0.1 to 30% by mol, in which
  (iv) the molar ratio of (i) said constituent units derived from said ethylene/(ii) said constituent units derived from said α-olefin of 3 to 20 carbon atoms is in the range of 40/60 to 92/8;

(C) said constituent unit derived from the chain polyene-group containing norbornene compound represented by the above formula (I) has a structure represented by formula (I) of claim 1, and said constituent unit derived from said chain polyene-group containing norbornene compound represented by the above formula (I-a) has a structure represented by the following formula (II-a):

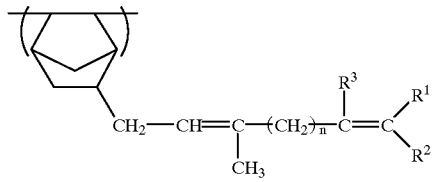

(II-a)

wherein n, $R^1$, $R^2$, and $R^3$ have the same meanings as in the formula (II) of claim 3; and (D) said copolymer has an intrinsic viscosity ($\eta$), as measured in Decalin at 135° C., of 0.05 to 10 dl/g.

6. A process for preparing an unsaturated ethylene copolymer as claimed in claim 5, comprising copolymerizing (i) ethylene, (ii) an α-olefin of 3 to 20 carbon atoms, and (iii) at least one chain polyene group-containing norbornene compound represented by the above formula (I) and at least one chain polyene group-containing norbornene compound represented by the above formula (I-a), in the presence of a catalyst formed from a transition metal compound, an organoaluminum compound and/or an ionizable ionic compound.

7. The chain polyene group-containing norbornene compound of claim 1 represented by the formula (I):

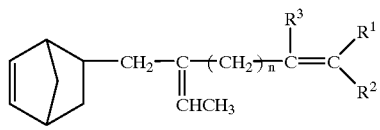

(I)

wherein n is an integer of 1 to 5, $R^1$ is an alkyl group of 1 to 2 carbon atoms, and $R^2$ is an alkyl group of 1 to 3 carbon atoms and $R^3$ is a hydrogen atom or an alkyl group of 1 to 3 carbon atoms.

8. The chain polyene group-containing norbornene compound represented by the formula (I) of claim 7, in which n is an integer of 1 to 3.

9. The process of claim 2 for preparing a chain polyene group-containing norbornene compound comprising reacting cyclopentadiene with a branched chain polyene compound represented by the formula (III):

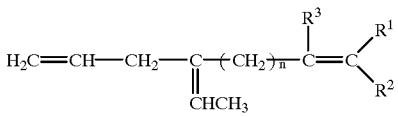

(III)

wherein n is an integer of 1 to 5, $R^1$ is an alkyl group of 1 to 2 carbon atoms, $R^2$ is an alkyl group of 1 to 3 carbon atoms and $R^3$ is a hydrogen atom and an alkyl group of 1 to 3 carbon atoms.

10. The process of claim 9 for preparing a chain polyene group-containing norbornene compound comprising reacting cyclopentadiene with a branched chain polyene compound represented by the formula (II) of claim 9 in which n is an integer of 1 to 3.

* * * * *